US010241106B2

(12) United States Patent
Sakairi

(10) Patent No.: US 10,241,106 B2
(45) Date of Patent: Mar. 26, 2019

(54) ATMOSPHERIC PRESSURE ION DETECTOR FOR OUTSIDE AIR MEASUREMENT

(71) Applicant: HITACHI, LTD., Tokyo (JP)

(72) Inventor: Minoru Sakairi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 197 days.

(21) Appl. No.: 14/241,717

(22) PCT Filed: May 27, 2013

(86) PCT No.: PCT/JP2013/064572
§ 371 (c)(1),
(2) Date: Feb. 27, 2014

(87) PCT Pub. No.: WO2014/192050
PCT Pub. Date: Dec. 4, 2014

(65) Prior Publication Data
US 2014/0346347 A1 Nov. 27, 2014

(51) Int. Cl.
*G01N 27/70* (2006.01)
*G01N 33/497* (2006.01)
*G01N 23/22* (2018.01)
*G01N 27/62* (2006.01)

(52) U.S. Cl.
CPC ......... *G01N 33/4972* (2013.01); *G01N 23/22* (2013.01); *G01N 27/70* (2013.01); *G01N 27/622* (2013.01)

(58) Field of Classification Search
CPC .............. G01N 27/62; G01N 33/4972; B60W 2540/24; H01J 49/165; H01J 49/025; H01J 49/0013; H01J 49/0018
See application file for complete search history.

(56) References Cited

U.S. PATENT DOCUMENTS

| | | | | |
|---|---|---|---|---|
| 5,965,882 A * | 10/1999 | Megerle | ................. | G01N 27/62 250/287 |
| 6,278,111 B1 | 8/2001 | Sheehan et al. | | |
| 6,512,224 B1 * | 1/2003 | Miller | ................. | H01J 49/0018 250/286 |
| 8,866,080 B2 * | 10/2014 | Bower | .................. | H01J 37/244 250/336.1 |
| 2003/0006778 A1 | 1/2003 | Aiki et al. | | |
| 2004/0155612 A1 * | 8/2004 | Krichtafovitch | .......... | B03C 3/68 315/500 |
| 2005/0085740 A1 * | 4/2005 | Davis | .................... | G01N 33/497 600/532 |
| 2008/0154179 A1 * | 6/2008 | Cantor | ................... | A61N 1/325 604/20 |

(Continued)

FOREIGN PATENT DOCUMENTS

| | | |
|---|---|---|
| JP | 2001-189199 A | 7/2001 |
| JP | 2003-014694 A | 1/2003 |

(Continued)

*Primary Examiner* — Brooke Purinton
(74) *Attorney, Agent, or Firm* — Mattingly & Malur, PC

(57) ABSTRACT

There is no small ion detecting apparatus that quickly and easily performs mass spectrometry under atmospheric pressure. Therefore, in order to solve the problem, an electrode arrangement and an electrode holding form for enabling water clusters in outside air to be detected with high sensitivity are provided. By using such solving means, it is possible to detect ions in a place having spatial constraints.

15 Claims, 28 Drawing Sheets

(56) References Cited

U.S. PATENT DOCUMENTS

| | | | |
|---|---|---|---|
| 2009/0121126 A1* | 5/2009 | Collings | H01J 49/427 250/282 |
| 2009/0224150 A1* | 9/2009 | Matyjaszczyk | G01N 27/622 250/282 |
| 2010/0301197 A1* | 12/2010 | Boyle | H01J 49/0409 250/252.1 |
| 2012/0037799 A1 | 2/2012 | Sakairi | |
| 2012/0081831 A1* | 4/2012 | Ishii | B03C 3/368 361/231 |
| 2012/0146798 A1* | 6/2012 | Dziekan | G01T 1/185 340/600 |
| 2012/0248306 A1 | 10/2012 | Sakairi | |
| 2014/0299759 A1* | 10/2014 | Allsworth | H01J 49/168 250/423 R |

FOREIGN PATENT DOCUMENTS

| | | |
|---|---|---|
| JP | 2007-114177 A | 5/2007 |
| JP | 2009-512494 A | 3/2009 |
| JP | 2010-256165 A | 11/2010 |
| JP | 2012-215484 A | 11/2012 |
| WO | 2007/046745 A1 | 4/2007 |
| WO | 2010-119568 A1 | 10/2010 |
| WO | 2011-045891 A1 | 4/2011 |

* cited by examiner

[FIG. 1]
(a)
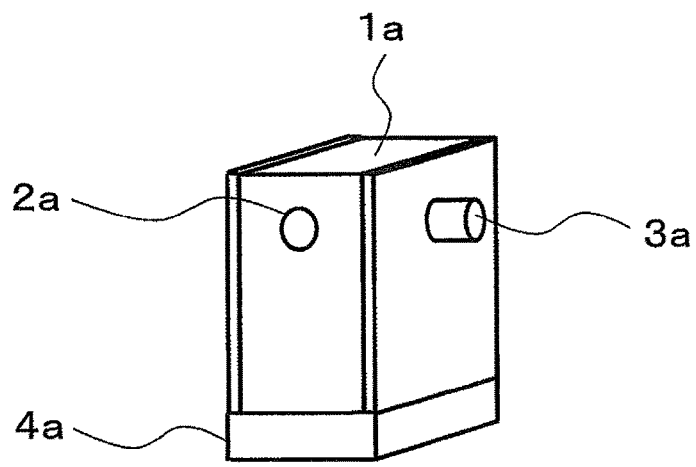
(b)
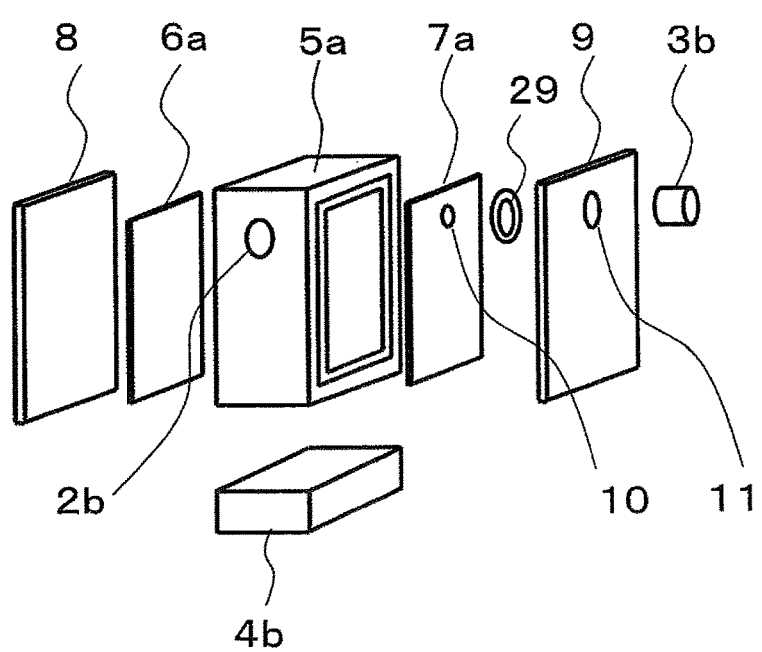

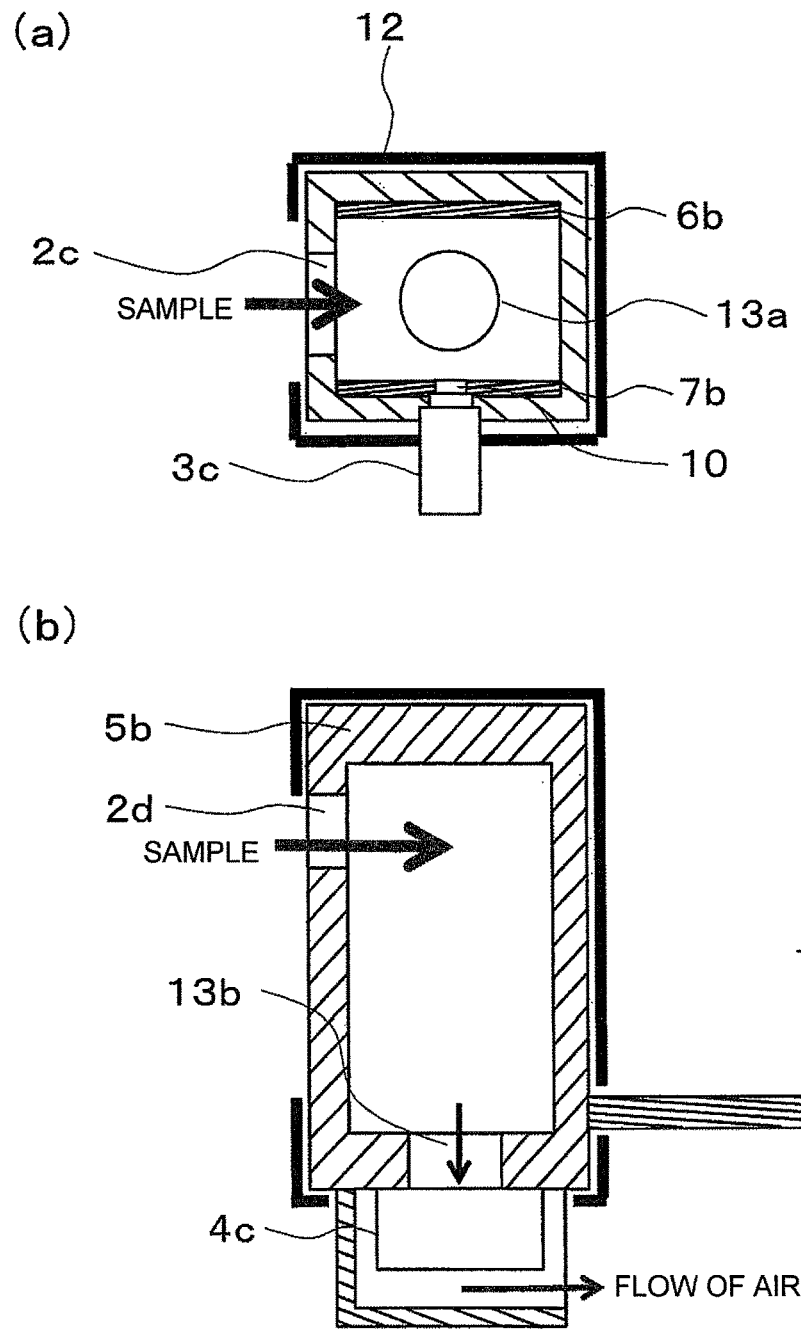
[FIG. 2]

[FIG. 3]
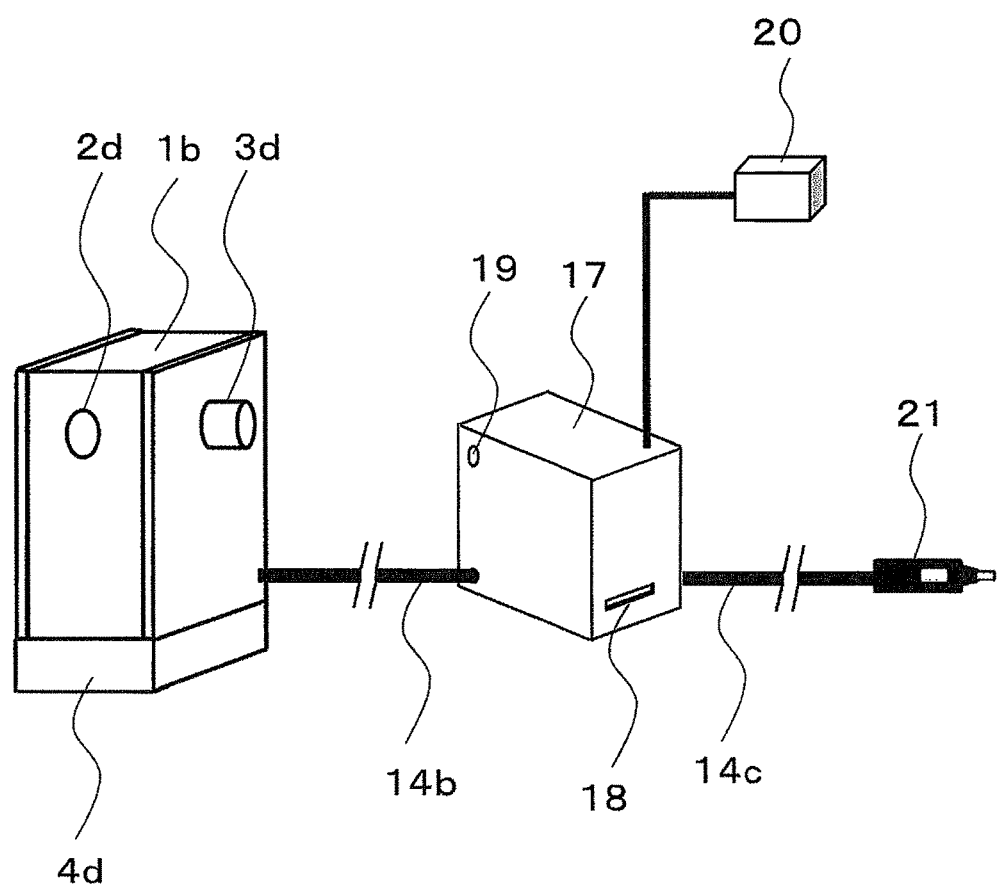

[FIG. 4]
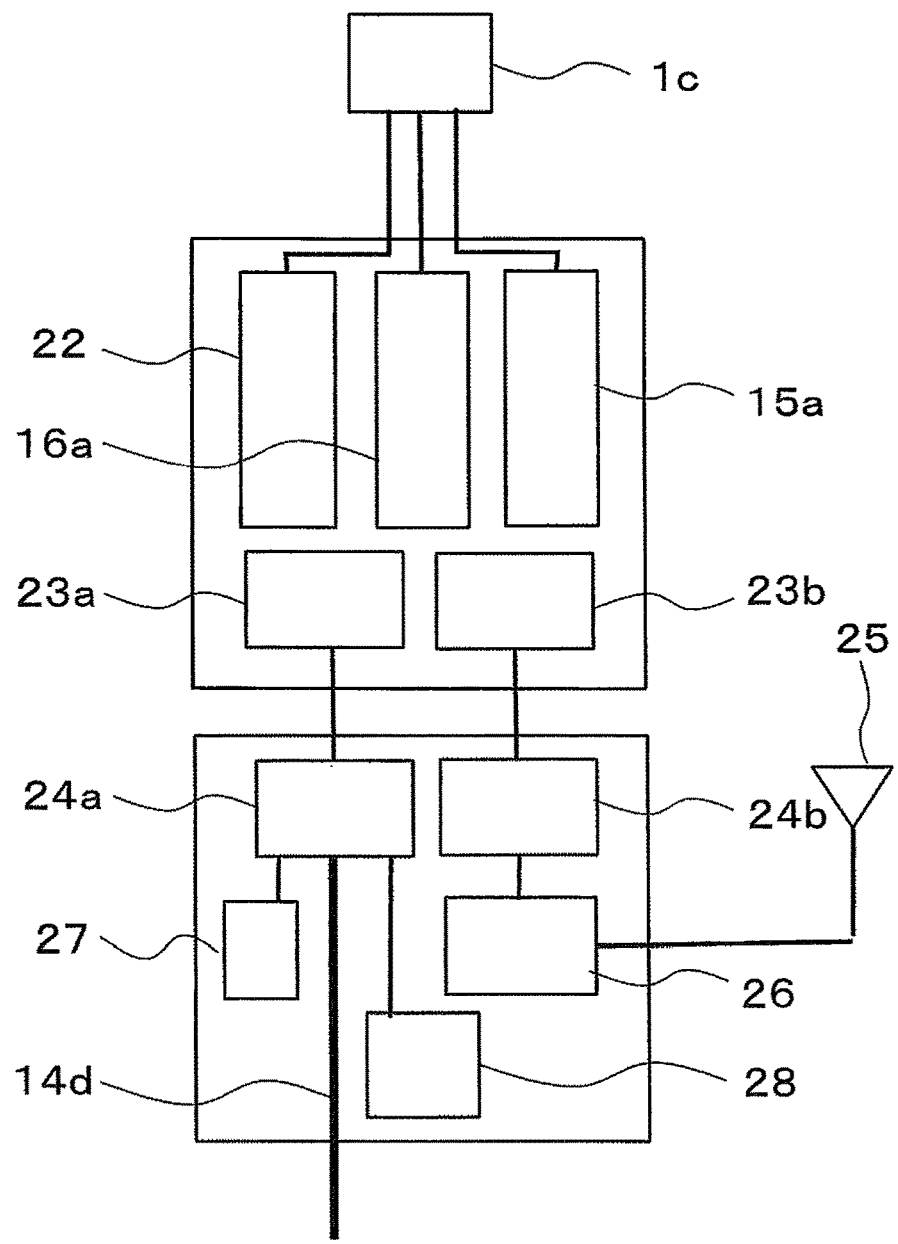

[FIG. 5]
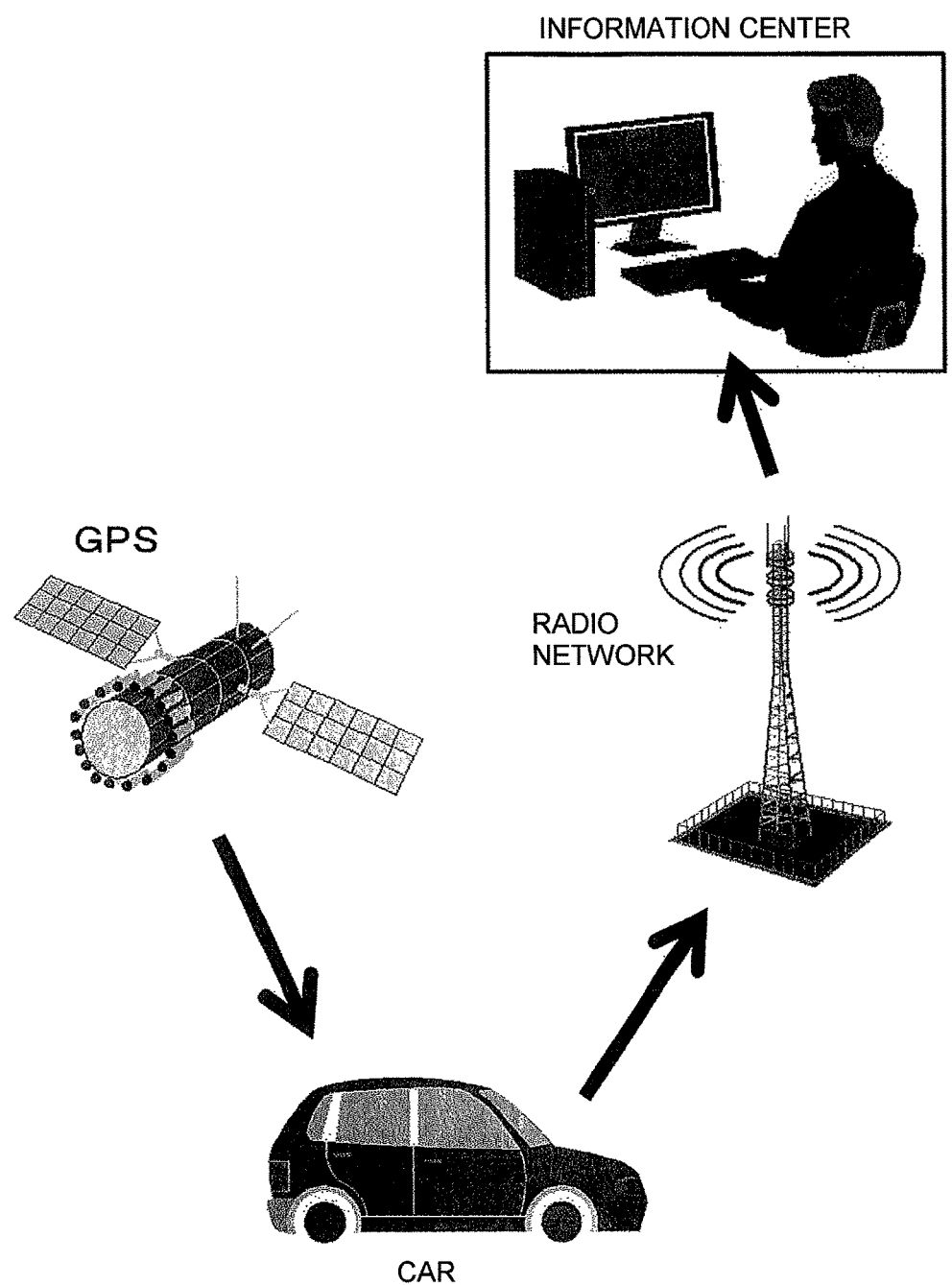

[FIG. 6]
(a)
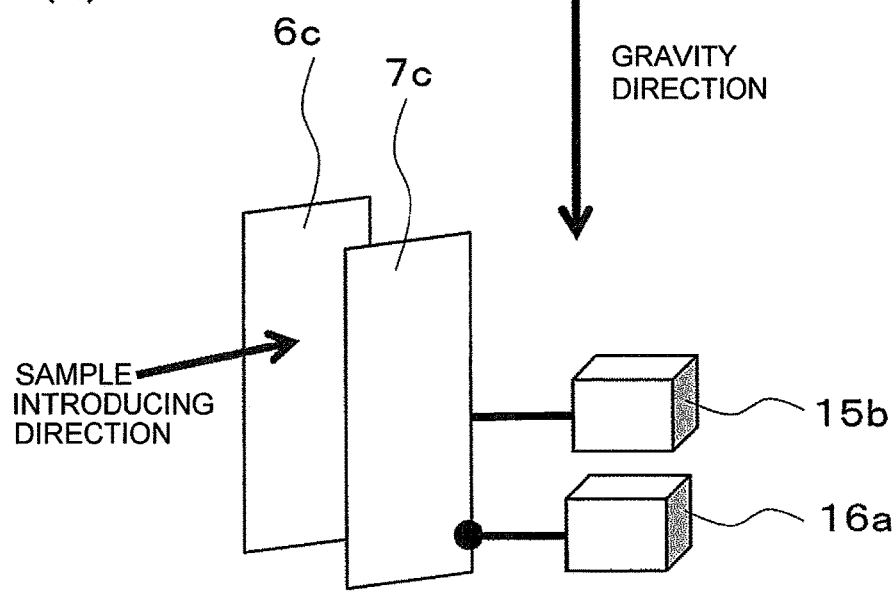
(b)
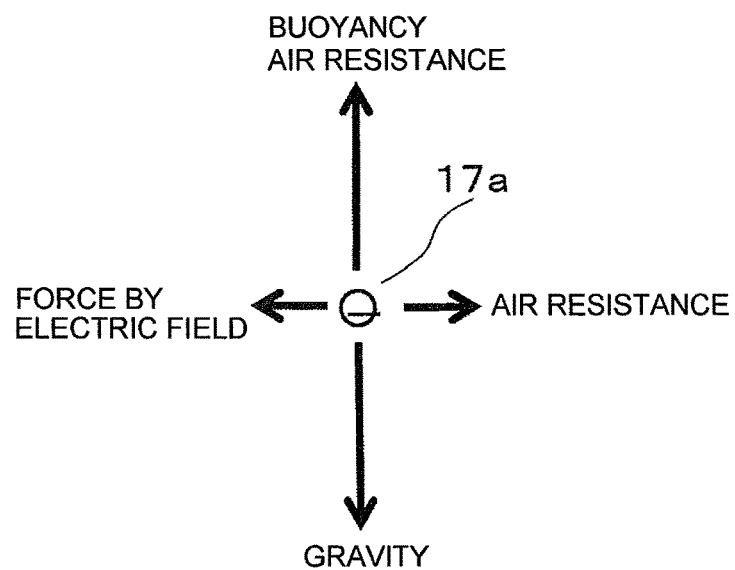

[FIG. 7]
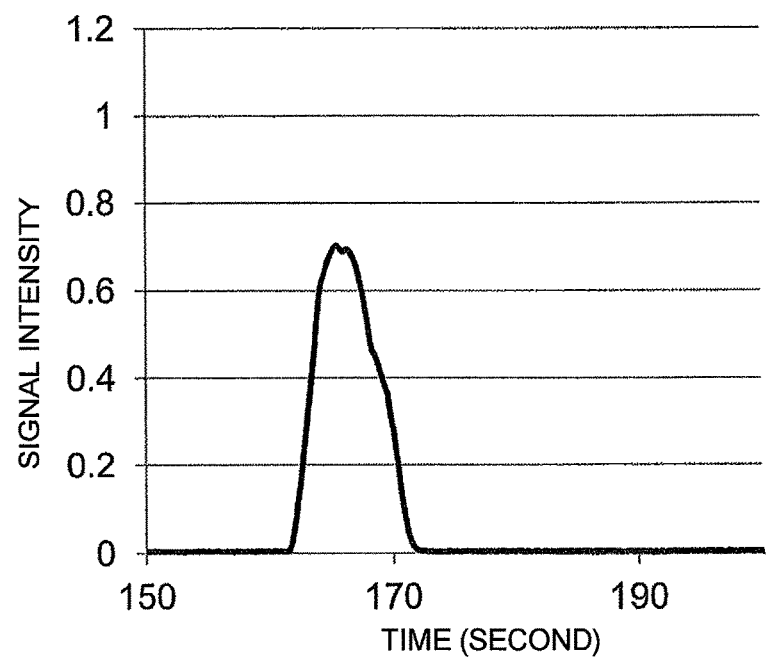

[FIG. 8]
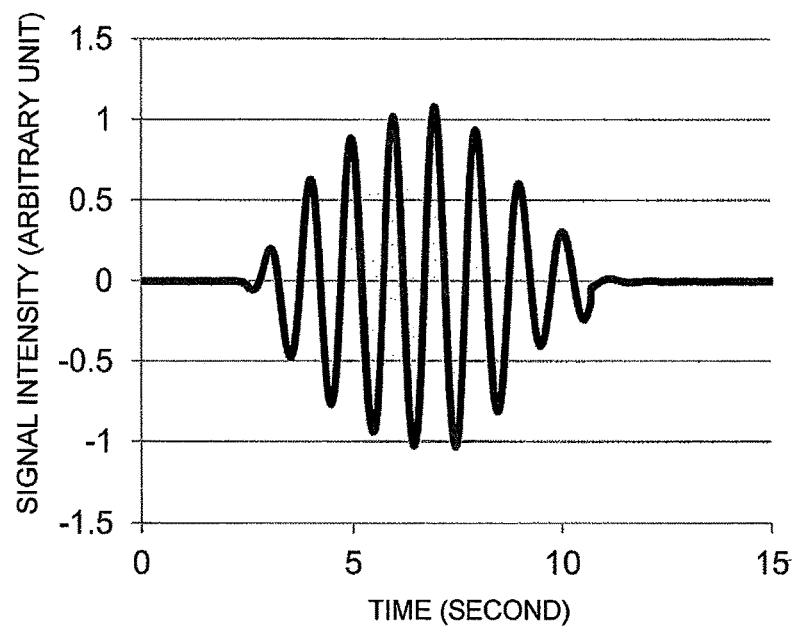

[FIG. 9]
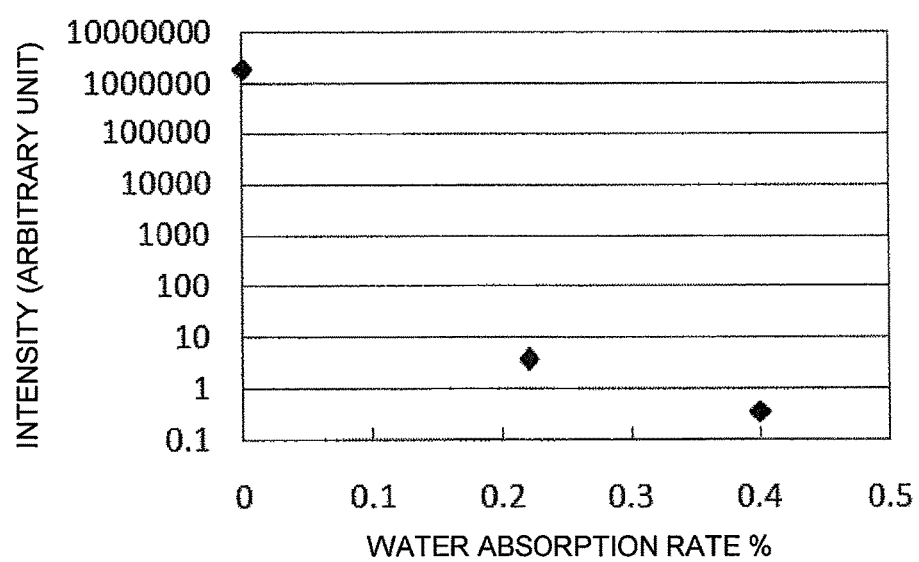

[FIG. 10]
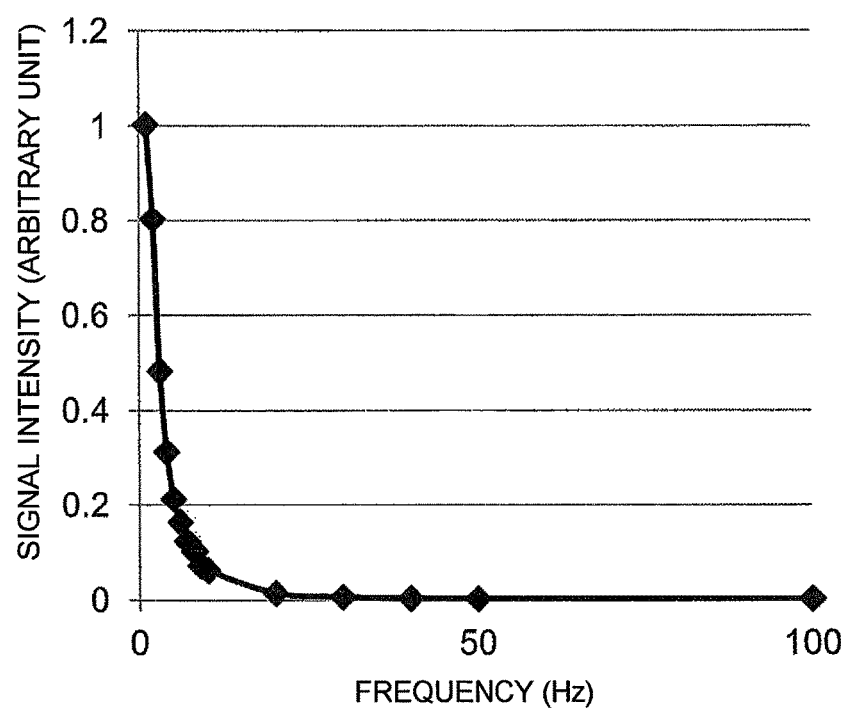

[FIG. 11(a)]
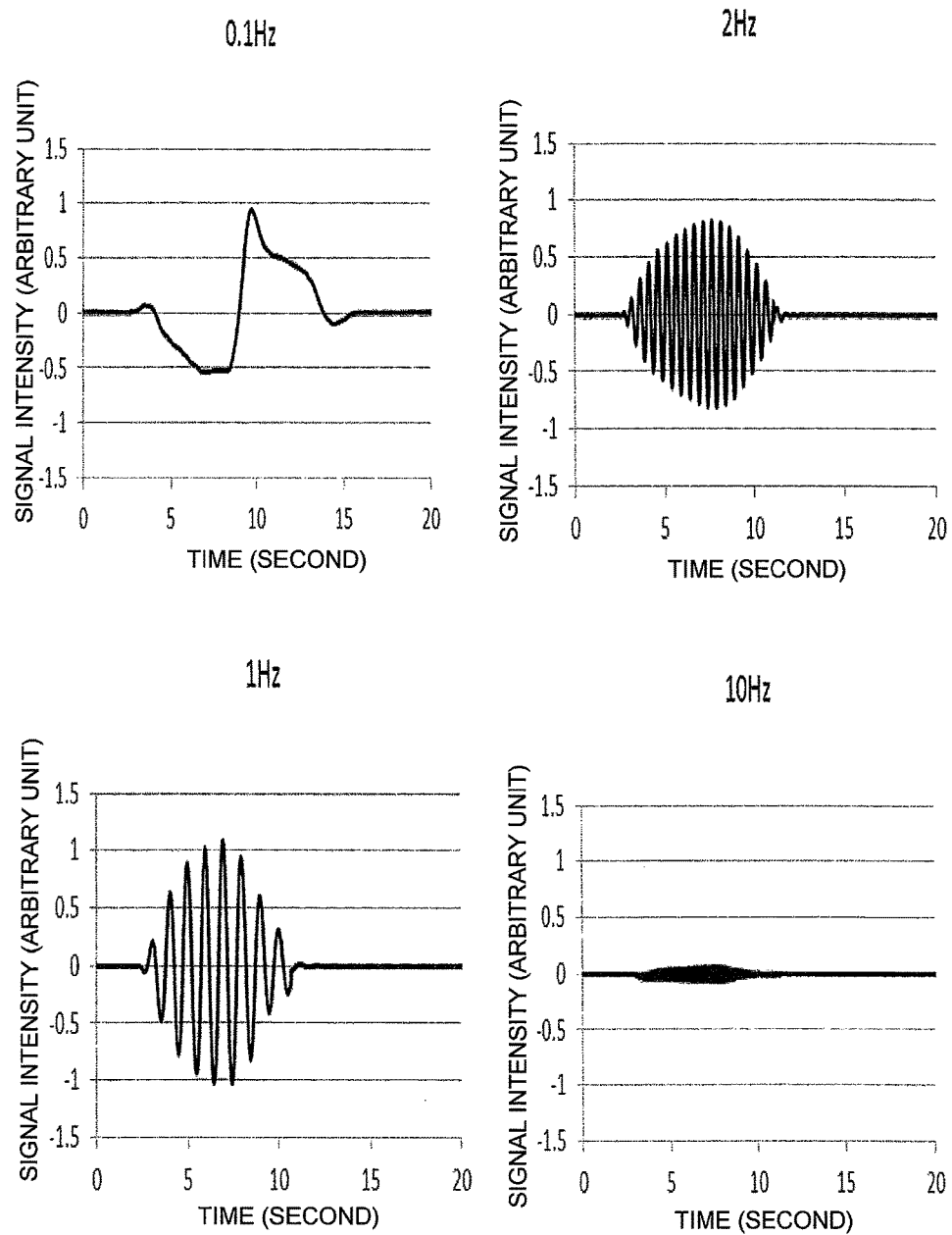

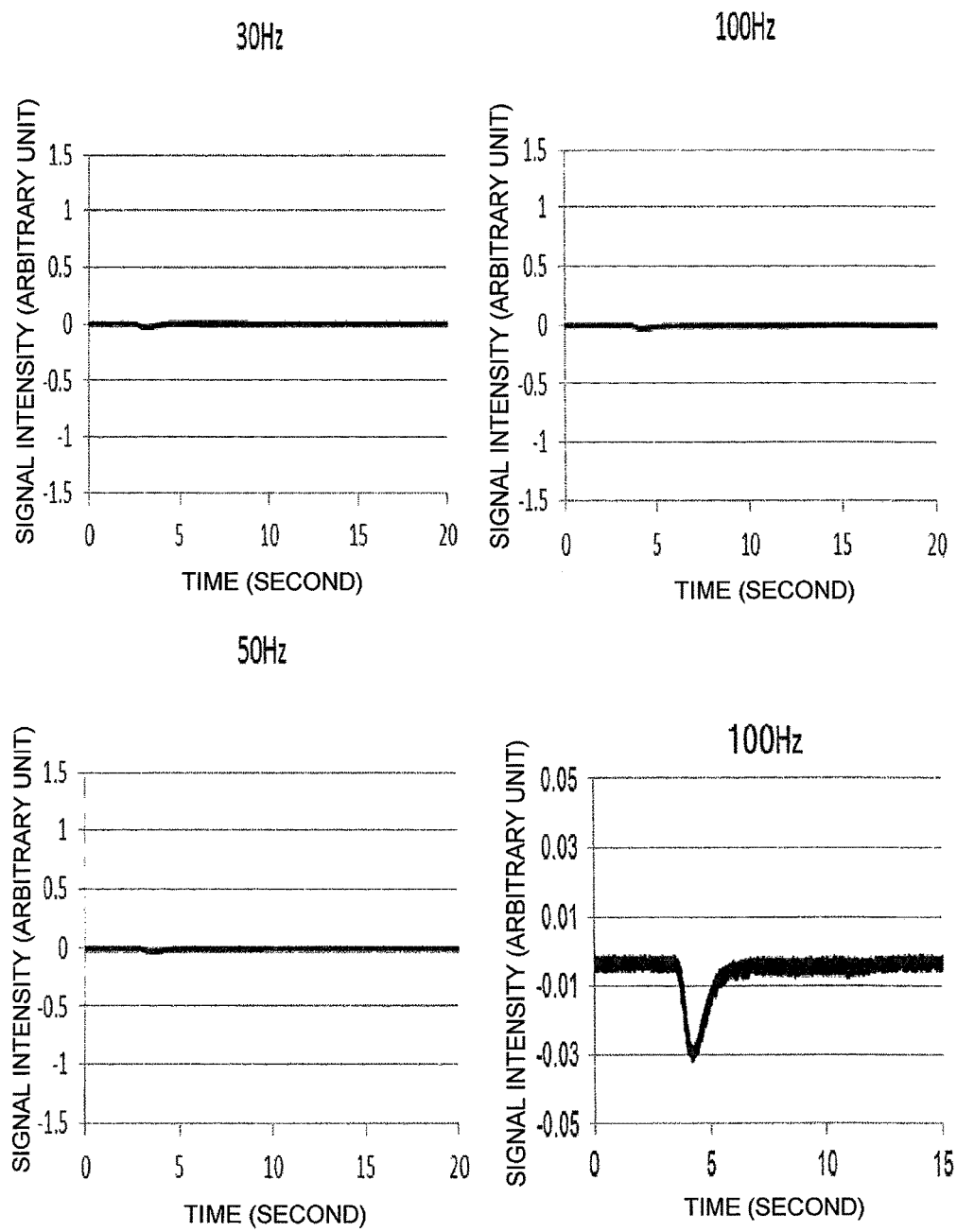
[FIG. 11(b)]

[FIG. 12]
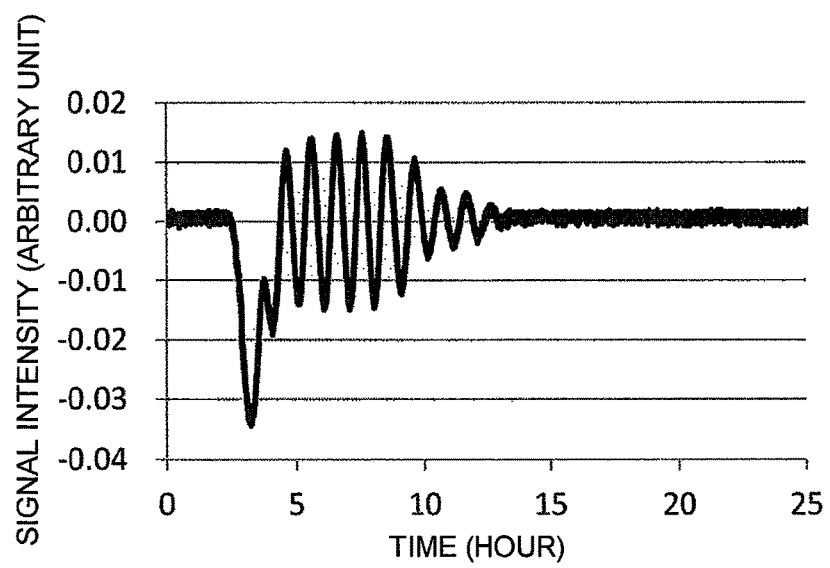

[FIG. 13]
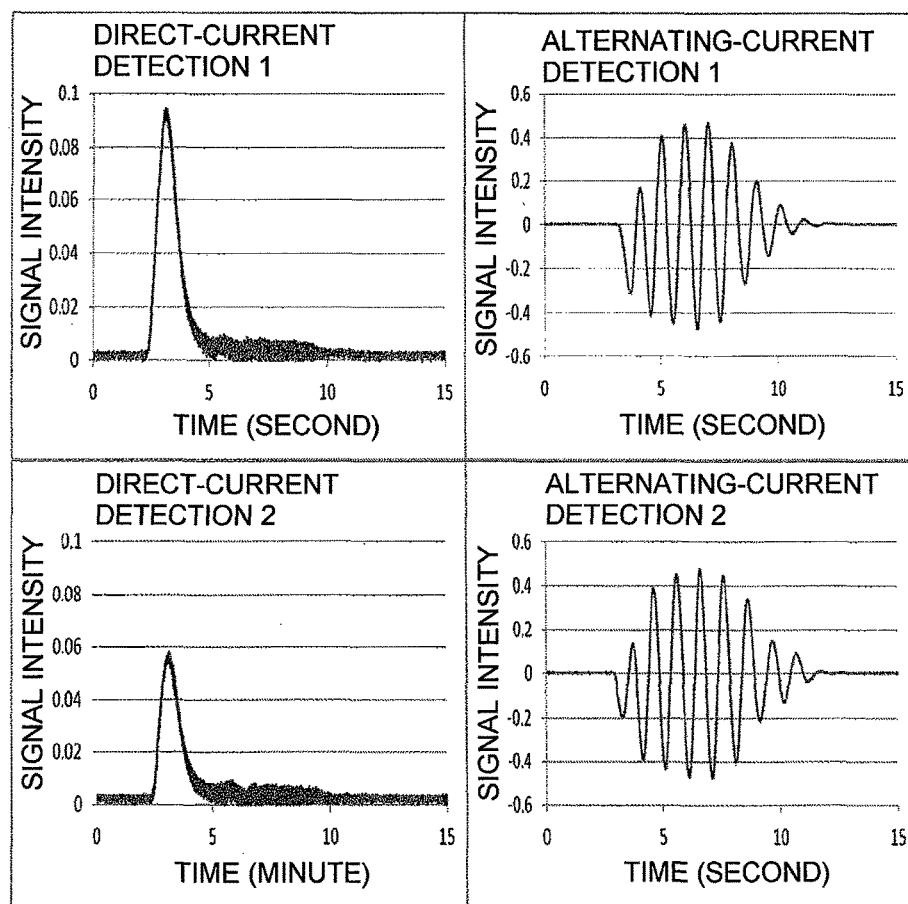

[FIG. 14]
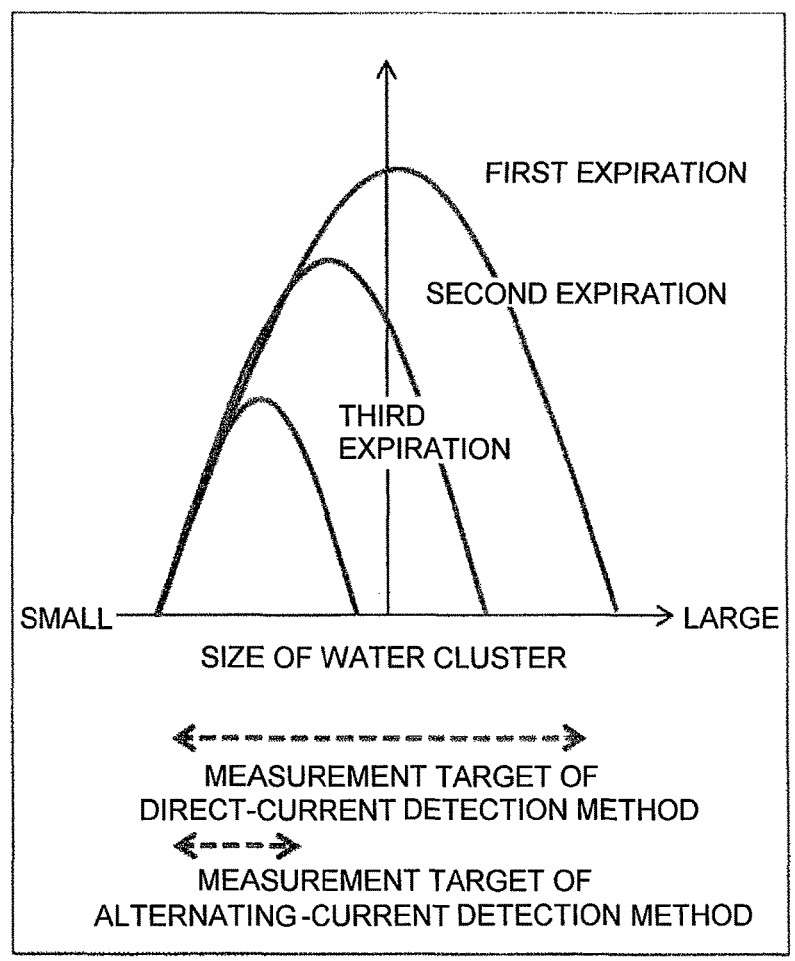

[FIG. 15]
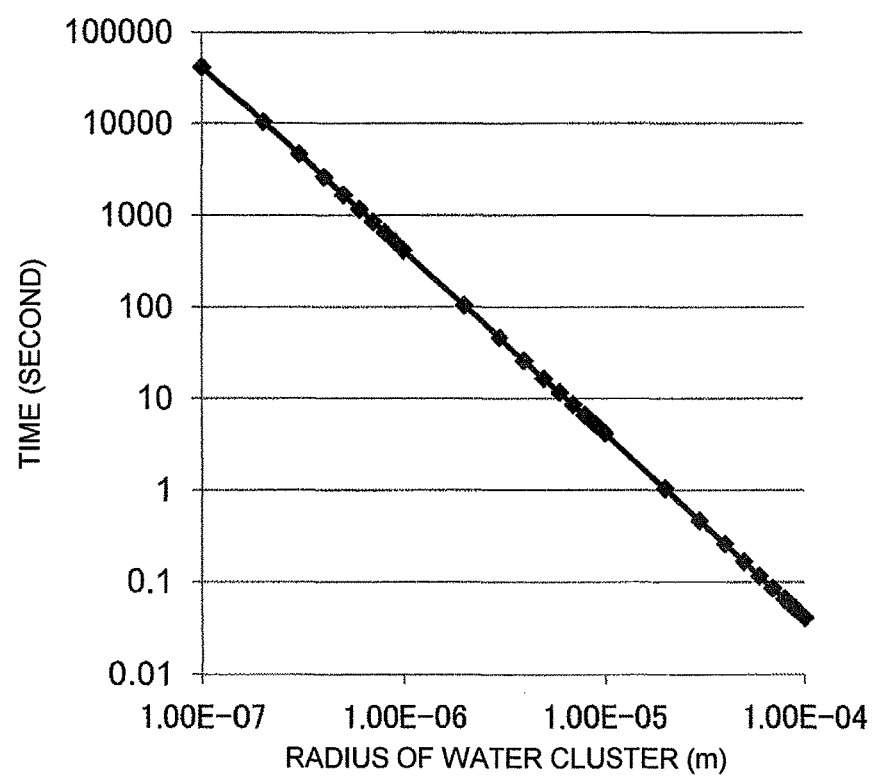

[FIG. 16]
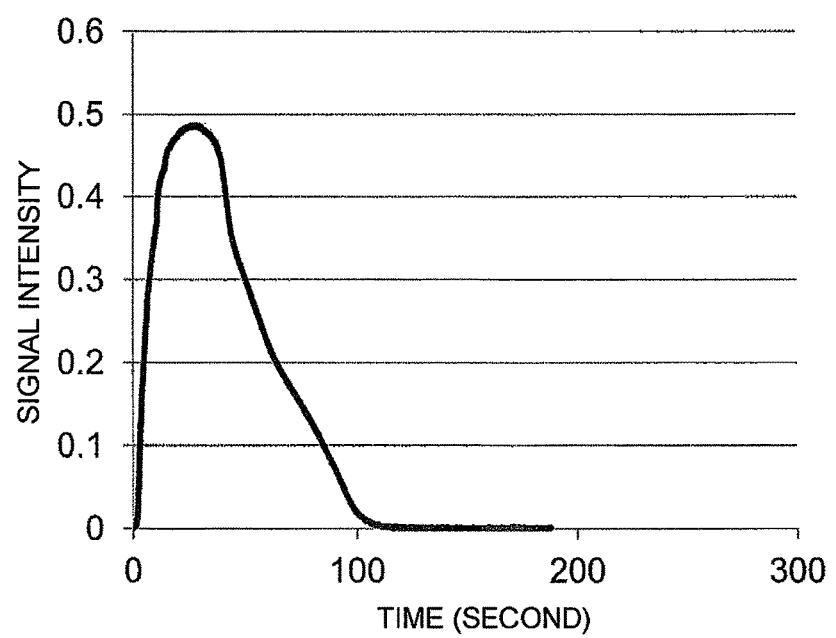

[FIG. 17]
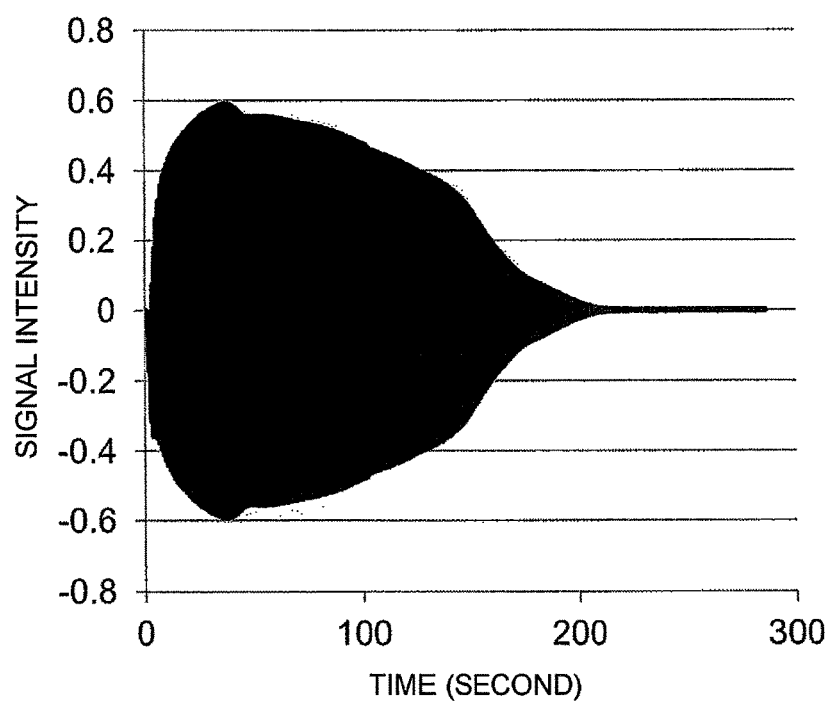

[FIG. 18]
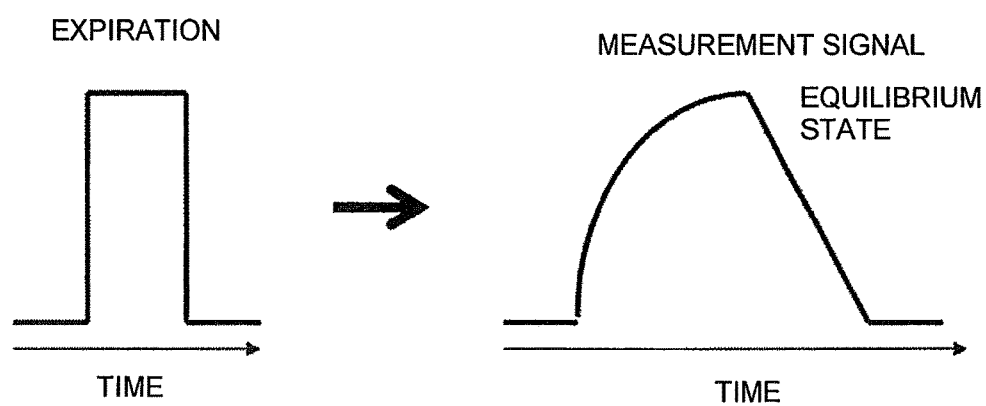

[FIG. 19]
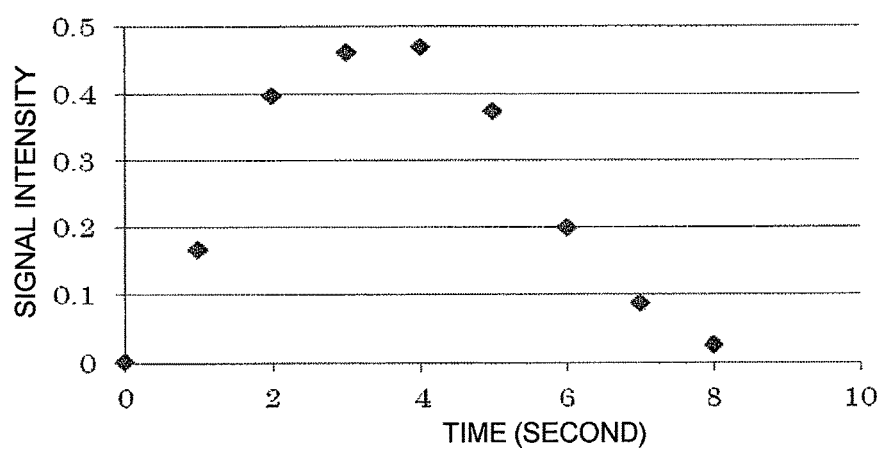

[FIG. 20]
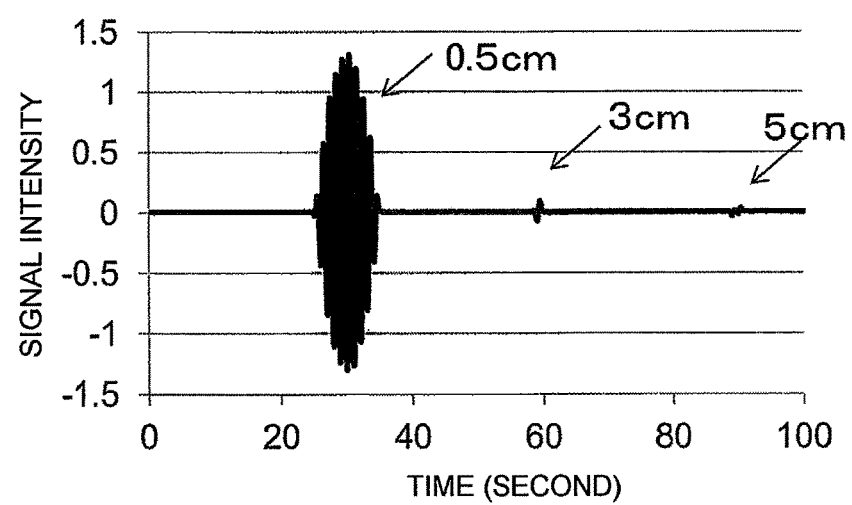

[FIG. 21]
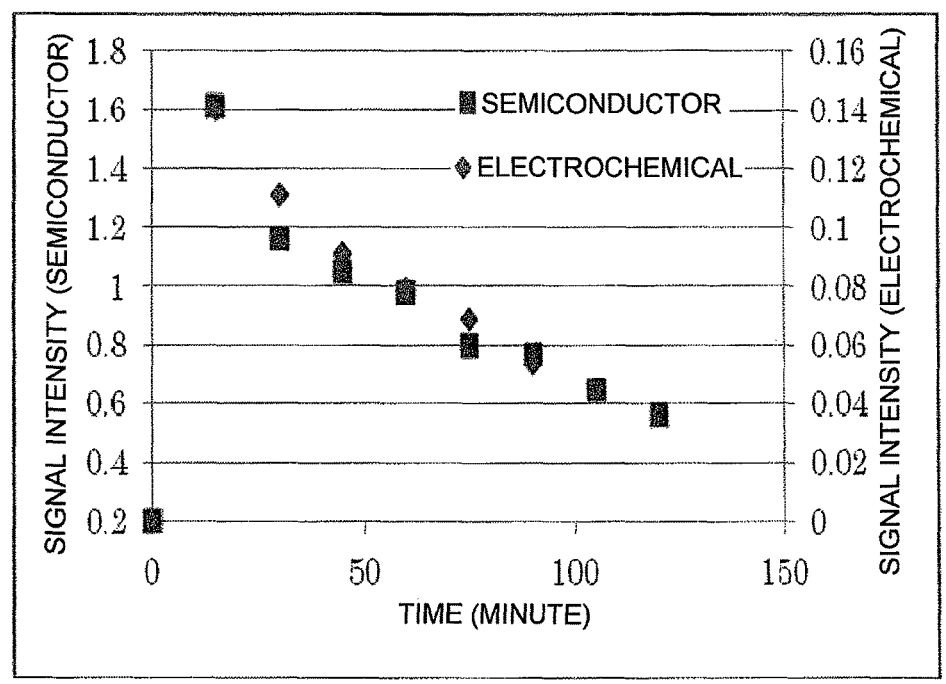

[FIG. 22]
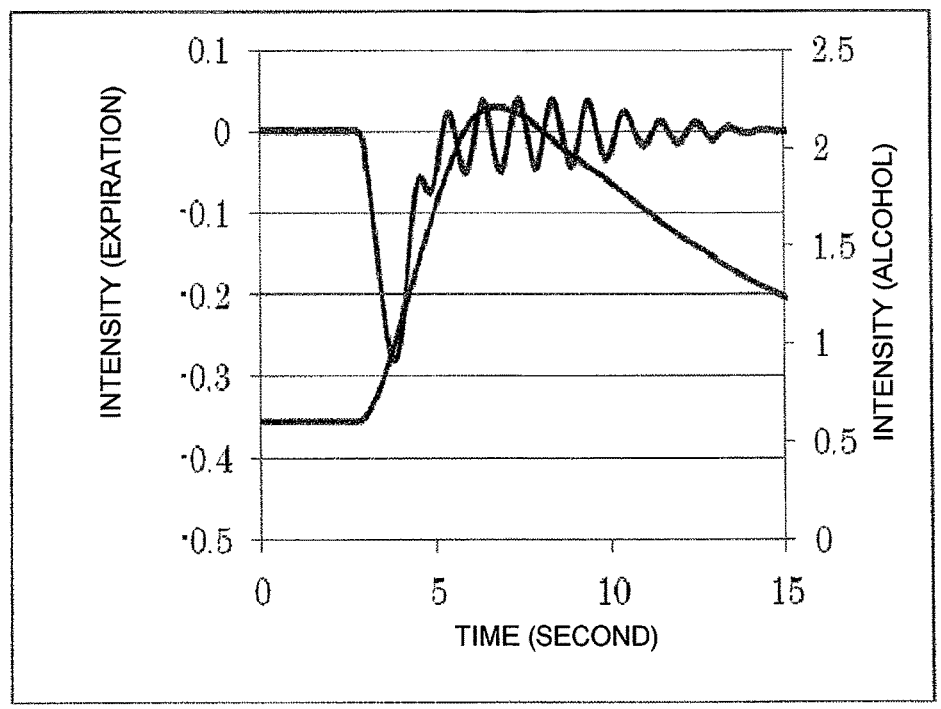

[FIG. 23]
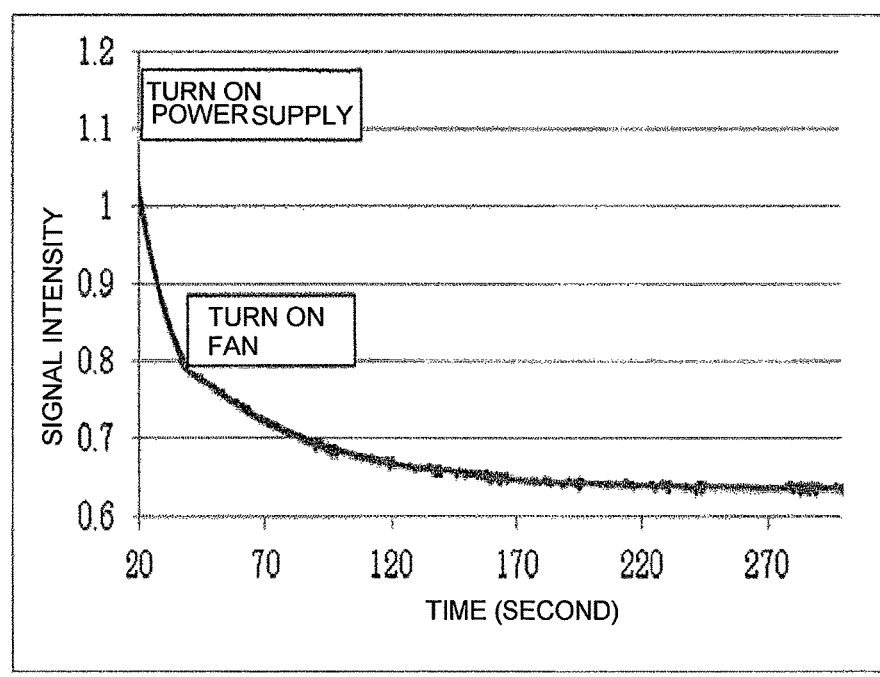

[FIG. 24]
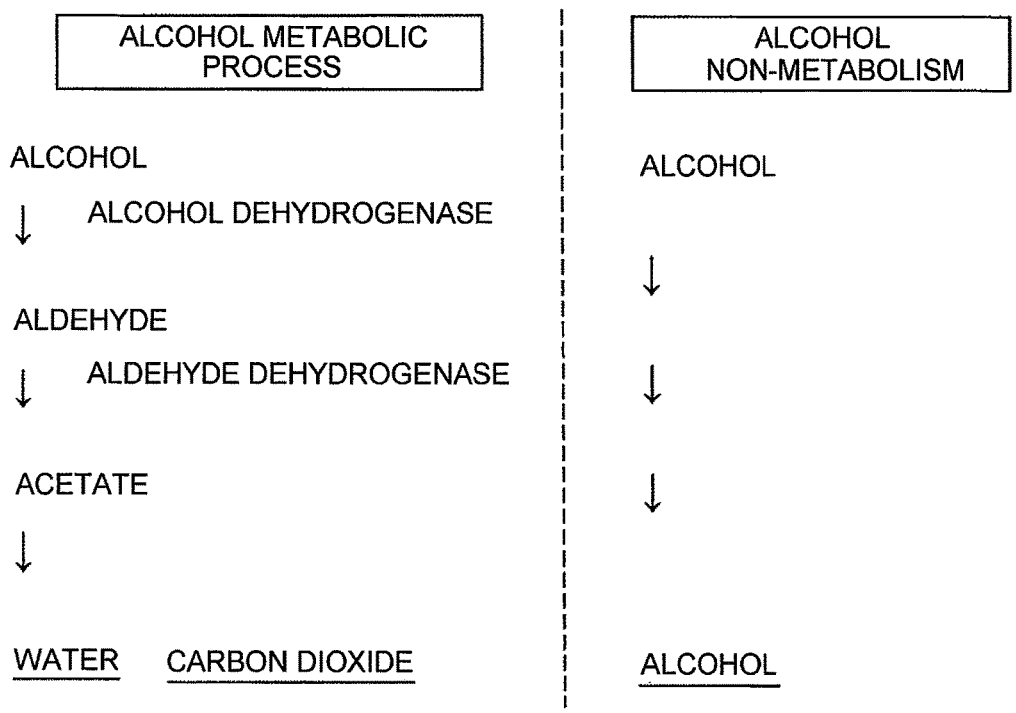

[FIG. 25]
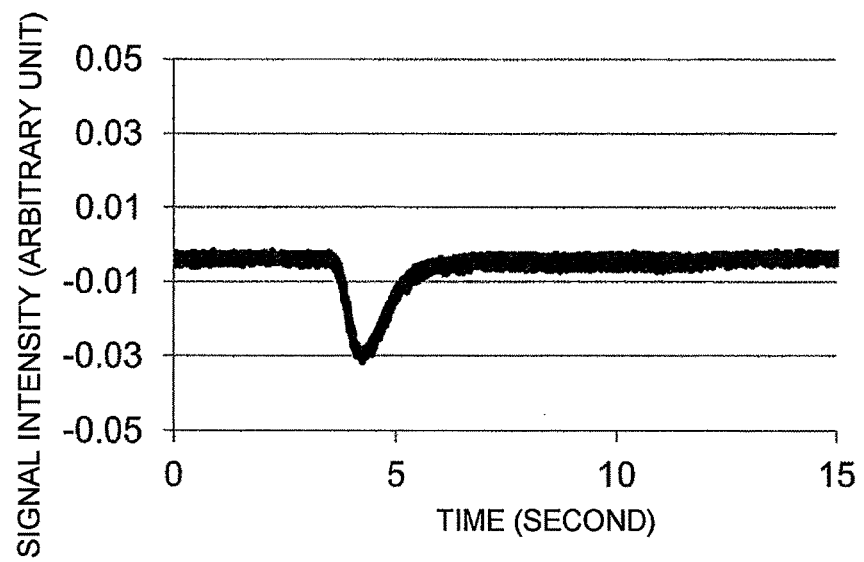

[FIG. 26]
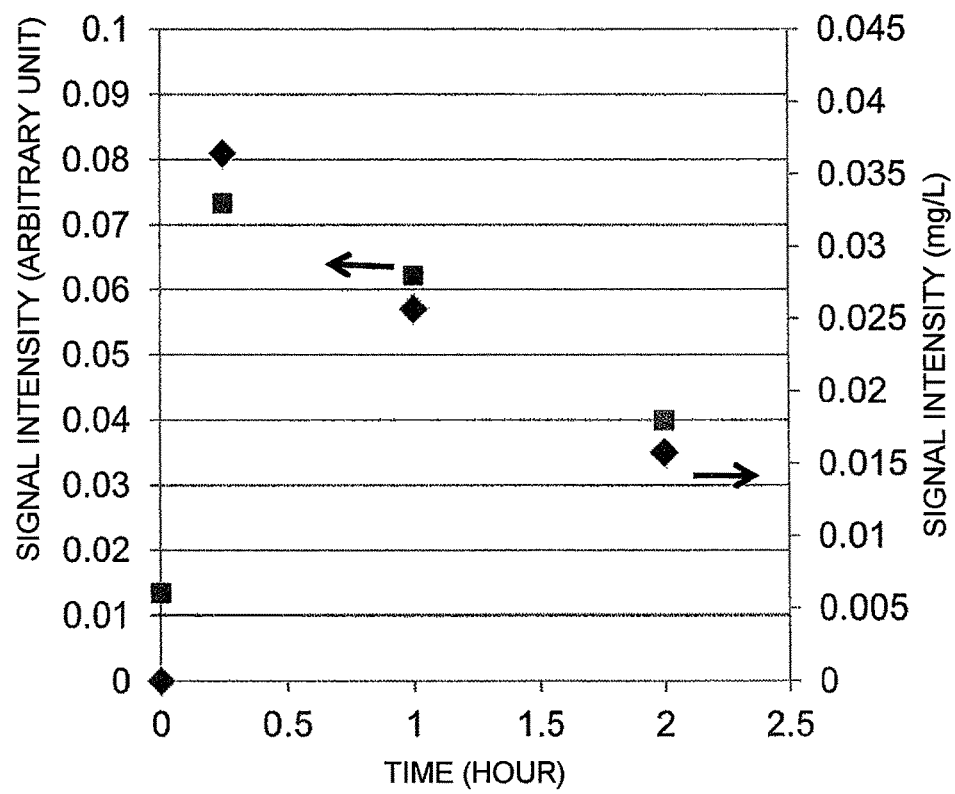

[FIG. 27]
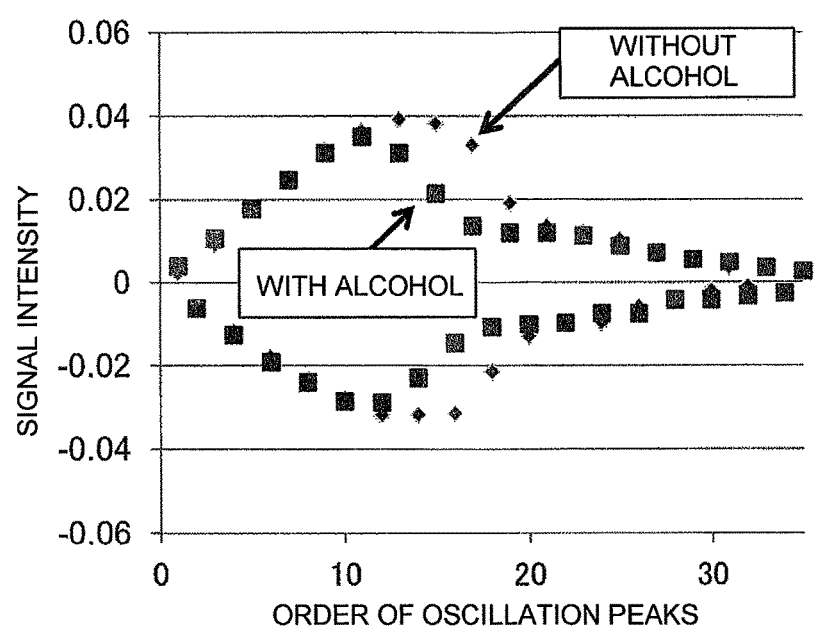

ATMOSPHERIC PRESSURE ION DETECTOR FOR OUTSIDE AIR MEASUREMENT

TECHNICAL FIELD

The present invention relates to a detecting apparatus based on ion detection under the atmospheric pressure. The present invention relates to, for example, a drunken driving preventing apparatus in a moving vehicle such as an automobile based on this detection technique. Further, the present invention relates to human measurement and outside air measurement.

BACKGROUND ART

In a technical field such as expiration detection and breath alcohol detection in the past, there is a method of ionizing a target object and detecting the target object using a mass spectrometer operated in a vacuum.

For example, PTL 1 discloses a method of introducing microdroplets generated by an ionization method called an electrospray method into a second chamber in a vacuum, promoting desolvation through collision with gas introduced in the chamber, and introducing desolvated ions to mass spectrometer.

In the method, it is necessary to provide a vacuum pumping system for putting an analysis environment under a high vacuum in order to analyze generated ions. The method is based on the premise that a mass spectrometer operating under such a high vacuum is used.

On the other hand, as a technique not including the vacuum pumping system, PTL 2 discloses an ion detecting apparatus that introduces outside air such as breath alcohol into a housing, the inside of which is under atmospheric pressure, and, in order to provide a potential difference between a voltage-applied electrode and a detection electrode arranged in the housing, applies a direct-current voltage to the voltage-applied electrode to deflect charged particles included in the introduced outside air, and detects a part of the charged particles with a detection electrode.

CITATION LIST

Patent Literature

PTL 1: U.S. Pat. No. 6,278,111
PTL 2: JP-A-2012-215484

SUMMARY OF INVENTION

Technical Problem

In the method disclosed in PTL 1, when the mass spectrometer operated at high vacuum is used as explained above, a mass number of ions can be measured and a highly accurate analysis can be performed. However, it is necessary to evacuate the inside of the mass spectrometer to a high vacuum equal to or lower than $10^{-2}$ Pa and substantially reduce the number of neutral molecules present in the mass spectrometer. Therefore, there is a problem in that an apparatus is increased in size because a vacuum pumping system such as a turbo-molecular pump and a rotary pump is provided.

On the other hand, in the method disclosed in PTL 2, it is possible to reduce the size of an apparatus because it is unnecessary to provide such a vacuum pumping system. However, in the method disclosed in PTL 2, since a direct-current voltage is applied to the voltage-applied electrode, the intensity of an expiration signal greatly changes according to a state of introduced expiration (e.g., the intensity of the expiration signal is greatly different between first expiration and second and subsequent expiration after deep respiration). Even if it is possible to recognize that the expiration signal is a signal by a human according to the shape of the expiration signal, it is difficult to use the signal intensity and the waveform of the expiration signal to determine whether expiration is correctly introduced.

Solution to Problem

An example of the present invention for solving the problems is a configuration explained below. An ion detecting apparatus in which the inside of a housing is under atmospheric pressure includes: an introducing port for introducing outside air into the housing; discharging means for discharging the introduced outside air; an ionization region section configured to form an ionization region for ionizing the outside air introduced from the introducing port; a voltage-applied electrode arranged in the ionization region; and a power supply configured to apply an alternating-current voltage to the voltage-applied electrode, the introducing port, the discharging means, the ionization region section, the voltage-applied electrode, and the power supply are being included in the housing. The ion detecting apparatus includes, in the ionization region, a detection electrode configured to detect an induction current generated by an outside air component ionized in the ionization region according to the application of the alternating-current voltage to the voltage-applied electrode.

Advantageous Effect of Invention

In detection of expiration (and the like, including outside air as a sample), it is possible to observe an expiration signal with high reproducibility without depending on a state of the expiration by using the alternating-current voltage. Therefore, there is a merit that it is possible to determine, from the intensity and the waveform of the expiration signal, whether the expiration is correctly introduced into the apparatus in respective measurements.

BRIEF DESCRIPTION OF THE DRAWINGS

FIG. 1(a) is a configuration diagram of a sensor unit of an apparatus of the present invention.

FIG. 1(b) is an exploded view showing components of the sensor unit in FIG. 1(a).

FIG. 2(a) is a sectional view of the sensor unit of the apparatus of the present invention.

FIG. 2(b) is side sectional view of the sensor unit of the apparatus.

FIG. 3 is a system configuration diagram of the apparatus of the present invention.

FIG. 4 is a circuit configuration diagram of the apparatus of the present invention.

FIG. 5 is an application example of the apparatus of the present invention.

FIG. 6(a) is a detection principle diagram of the apparatus of the present invention.

FIG. 6(b) shows direction arrows illustrating a detection principle of the present invention.

FIG. 7 is a detection example of expiration by a direct-current voltage in the apparatus of the present invention.

FIG. 8 is a detection example of expiration by an alternating-current voltage in the apparatus of the present invention.

FIG. 9 is dependency on material water absorption rate of expiration signal intensity in the apparatus of the present invention.

FIG. 10 is frequency dependency of the expiration signal intensity in the apparatus of the present invention.

FIG. 11(*a*) is an example of frequency dependency of an expiration signal in the apparatus of the present invention.

FIG. 11(*b*) is an example of the frequency dependency of the expiration signal in the apparatus of the present invention.

FIG. 12 is a measurement example by an alternating-current voltage method in the apparatus of the present invention.

FIG. 13 is an example showing signal intensity in a direct-current voltage method and an alternating-current voltage method in the apparatus of the present invention.

FIG. 14 is a diagram for explaining reproducibility of a signal in the alternating-current voltage method in the apparatus of the present invention.

FIG. 15 is a diagram showing a relation between a radius of water clusters and time until the water clusters reach an electrode lower end.

FIG. 16 is a diagram showing a signal observed by the direct-current voltage method when a fan is not driven in the apparatus of the present invention.

FIG. 17 is a diagram showing a signal observed by the alternating-current voltage method when the fan is not driven in the apparatus of the present invention.

FIG. 18 is a diagram showing a relation between introduced expiration and an observed waveform in the apparatus of the present invention.

FIG. 19 is a diagram showing an intensity change of peaks of an expiration signal observed by the alternating-current voltage method in the apparatus of the present invention.

FIG. 20 is a diagram showing mouth-to-expiration sensor distance dependency of an expiration signal in the apparatus of the present invention.

FIG. 21 is a diagram showing changes with time of an expiration signal and an alcohol signal after drinking in the apparatus of the present invention.

FIG. 22 is a diagram showing a simultaneous measurement example of an expiration signal and an alcohol signal after drinking in the apparatus of the present invention.

FIG. 23 is a diagram showing a signal change of a semiconductor alcohol sensor during fan driving in the apparatus of the present invention.

FIG. 24 is a diagram showing a metabolic process of alcohol.

FIG. 25 is a diagram showing detection of negative ions measured without a voltage in the apparatus of the present invention.

FIG. 26 is a diagram showing a change with time of negative ion intensity after drinking in the apparatus of the present invention.

FIG. 27 is a diagram showing a difference between expiration signals due to presence or absence of alcohol in the present invention.

DESCRIPTION OF EMBODIMENTS

First Embodiment

In an embodiment explained below, there is provided an example of an analysis method for causing a portion where ions are detected to operate under atmospheric pressure and performing separation of ions according to a method different from the related art in the past by using, as forces acting on the ions, action of not only a force by an electric field but also air resistance, buoyancy, and gravity that are characteristics in causing the portion to operate under atmospheric pressure.

In order to provide an analysis method for effectively using the action by the force by the electric field and the gravity on the ions, it is also effective to cause the force of the electric field to act in a direction different from the gravity and separate the ions (e.g., the directions of the gravity and the force by the electric field are different by 90 degrees). Further, when the portion is caused to operate under atmospheric pressure to detect the ions, it is easy to arrange a plurality of detecting units having the same structure and improve detection sensitivity. Note that an ammeter operating under atmospheric pressure is used for the ion detection.

In the mass spectrometer in the past, a sample has to be introduced after the mass spectrometer reaches a certain level of a vacuum. However, in the apparatus operating under atmospheric pressure, it is possible to immediately introduce a sample and start measurement if a power supply is turned on.

When outside air can be detected by the simple method in this way, it is possible to detect expiration in a place having spatial constraints. For example, it is possible to perform drunken driving prevention based on an expiration alcohol test in the interior of an automobile.

On the other hand, water clusters present in expiration can change to both of water clusters having positive charges and water clusters having negative charges according to an electric field. Therefore, it is possible to detect a positive or negative electric current by changing the polarity of an applied direct-current voltage. Further, by using this characteristic, when water cluster ions having charges are detected, it is possible to use not only a direct-current voltage but also an alternating-current voltage.

As a detection system, a specific configuration example for detecting expiration alcohol is shown in FIG. 1(*a*). In a sensor unit 1*a*, a sample introducing port 2*a* (having a diameter of about 5 to 10 mm) for introducing expiration, an alcohol sensor head 3*a* (a semiconductor sensor, etc.) for detecting alcohol and the like, and an exhaust fan section 4*a* for exhausting a part of the introduced expiration to the outside of the sensor unit are provided. A small DC fan (having an air capacity of about 0.1 to 0.01 m³/minute) and the like can be used for the sensor unit 1*a*. In FIG. 1(*b*), components of the sensor unit 1*a* are shown. A voltage-applied electrode 6*a* and a detection electrode 7*a* are arranged on both sides of an ionization region section 5*a* including a sample introducing port 2*b*. Further, a voltage-applied electrode holder 8 and a detection electrode holder 9, which are electrode holding members for holding these electrodes and electrically insulating the electrodes, are arranged.

Under the ionization region section 5*a* having a space functioning as an ionization region on the inside, an exhaust fan 4*b* functioning as evacuating means for evacuating the ionization region section 5*a* is provided. It is possible to detect alcohol using an alcohol detection hole 10 of the detection electrode 7*a* of the sensor unit 1*a* and an alcohol sensor head 3*b* fit in an alcohol sensor support hole 11 of the detection electrode holder 9 via an insulating material 29 for insulating the detection electrode 7*a* and the alcohol sensor head 3*b*. That is, it is possible to detect alcohol inside an ionization region by exposing the alcohol sensor head 3b, which is a detection surface, to the inside of the ionization region.

In FIG. 2(a), a sectional view of the sensor unit viewed from above is shown. Outside air (e.g., expiration serving as a sample) introduced from a sample introducing port 2c is introduced into the ionization region surrounded by a voltage-applied electrode 6b and a detection electrode 7b and exhausted to the outside by an exhaust fan through an exhaust port 13a.

FIG. 2b is a sectional view of the sensor unit viewed from a side. A sample introduced from a sample introducing port 2d collides against a wall of an ionization region section 5b and moves downward. Then, apart of expiration is exhausted to the outside of the system from an exhaust port 13b by an exhaust fan 4c. A blower fan is described as an example of exhausting means. However, it is not always necessary to provide a fan. It is also possible to adopt a form for sucking the air from the outside. It is also possible to provide a sensor cover 12 in the sensor unit. An obtained signal is sent to a measurement control unit via a cable 14a.

In a measurement control unit 17 shown in FIG. 3, an indicator lamp 19 indicating that the measurement control unit 17 is operating and a memory card slot 18 for inserting a memory card for storing obtained data are provided. In this example, as an example of a storage device, the memory card and the memory card slot 18 are shown. However, the storage device is not limited to this. It goes without saying that the storage device may be an external storage medium or a storage device of an embedded type. It is effective to provide a GPS antenna unit 20 for obtaining positional information of a mobile body. A power supply voltage supplied to a sensor unit 1b and the measurement control unit 17 is supplied via a cable 14b. In an automobile or the like, the power supply voltage is supplied via a power inverter 21. It is also possible to use a normal power supply for home use and a storage battery. In addition, an alcohol sensor head 3d is provided along with an exhaust fan 4d.

In FIG. 4, a circuit configuration of a sensor on the inside of the measurement control unit 17 is shown. An example is shown in which an alternating-current voltage is supplied to a voltage-applied electrode of a sensor unit 1c or a voltage is supplied to the voltage-applied electrode from a sensor power supply 15a having a switching function for a direct-current voltage and an alternating-current voltage.

A signal of expiration obtained by the sensor unit 1c is amplified and converted into a voltage by a sensor amplifier 16a and sent to a CPU 23a. Similarly, when an alcohol sensor is provided, a signal of alcohol obtained by an alcohol sensor head is amplified by an alcohol sensor amplifier 22 and sent to the CPU 23a. Further, positional information obtained by a GPS antenna 25 and a GPS receiver 26 is sent to a CPU 23b. Information to be finally obtained is the signal of the expiration, the signal of the alcohol, the positional information, and information concerning time (correction of an internal clock is carried out by acquiring the information from a GPS signal). The information is stored in the storage device.

As a specific example, the information is accumulated in the memory card via a memory card interface 27. Further, it is effective to provide a speaker 28 for sound guidance carried out for a subject in actual measurement. Electric power is supplied to the sensor circuit via a power supply cable 14d. In FIG. 5, information obtained by a radio network is sent to an information sensor. However, it is also effective to utilize the information obtained in such a form.

In FIG. 6(a) and FIG. 6(b), a detection principle of the present invention is shown. A potential difference is provided between a voltage applied-electrode 6c and a detection electrode 7c by a sensor power supply 15b. At this point, when expiration including water clusters is introduced into a space between a voltage applied-electrode 6c and a detection electrode 7c from a direction of an arrow, as shown in FIG. 6(b), air resistance, buoyancy, gravity, and a force by an electric field act on small-diameter water clusters having charges.

According to a relation among these forces, when a positive direct-current voltage is applied to the voltage-applied electrode 6c, only water clusters having positive charges deflect and collide against a detection electrode 7c and a positive electric current is detected. Therefore, the water clusters deflecting and colliding against the detection electrode 7c are small-diameter water clusters having charges. Large-diameter water clusters having charges do not collide against the detection electrode 7c and are not detected. An example of measurement of an expiration signal performed using the direct-current voltage (a direct-current voltage method) is shown in FIG. 7. As this example, an example in which outside air is detected in a noncontact and noninvasive manner, specifically, an example in which expiration is detected is explained. It goes without saying that not only expiration but also outside air can be introduced and detected.

On the other hand, when an alternating-current voltage is used, water clusters are polarized and ionized according to a temporal change of the voltage. A force generated by an electric field applied to the water clusters having charges cyclically changes. When the force changes, an induction current is generated. The induction current is detected by a detection electrode.

An example of measurement of an expiration signal performed using the alternating-current voltage (an alternating-current voltage method) is shown in FIG. 8. A measurement condition is the alternating-current voltage (having a frequency of 1 Hz and an effective voltage of 30V). In the alternating-current voltage method, unlike the direct-current voltage method, it is seen that expiration signal intensity fluctuates with time according to the frequency 1 Hz. In the alternating-current voltage method, water clusters having charges in an ionization region do not collide against a wall of an electrode or the like. An induction current generated by oscillation of a large number of water clusters having charges is detected. Therefore, measurement at a low voltage is possible.

In order to observe a signal concerning water clusters in expiration using an alternating-current voltage, it is important to optimize the material of the ionization region section and a frequency to be applied. First, the material of the ionization region section 5a shown in FIG. 1 is explained.

In FIG. 9, a difference in the intensity of an expiration signal due to a difference in a material used for the ionization region section 5a is shown. The voltage-applied electrode 6a and the detection electrode 7a have to be formed of metal such as stainless steel. The material of the ionization region section 5a set around the voltage-applied electrode 6a and the detection electrode 7a and exposed to water clusters is extremely important. In an apparatus that detects small-diameter water clusters, when a material that easily absorbs water is used, water clusters are easily absorbed by the material, water clusters involved in detection decrease, and detection sensitivity substantially decreases. In a graph shown in FIG. 9, a water absorption rate of the material is plotted on the horizontal axis and the intensity of an expiration signal is plotted on the vertical axis. The graph shows a result obtained when an expiration signal is measured using, for the ionization region section 5a, a material having a water absorption rate of 0 such as machinable ceramic, a material having a water absorption rate of about 0.25 such as polyacetal, and a material having a water absorption rate of about 0.4 such as polyvinyl chloride. That is, whereas the expiration signal is slightly detected at the water absorption rate of about 0.4, the expiration signal starts to be clearly observed at the water absorption rate of about 0.25 and, when the water absorption rate decreases to 0, the expiration signal intensity greatly rises compared with the expiration signal intensity at the water absorption rate of 0.4.

This indicates that the material of the ionization region section 5a exposed to water clusters is extremely important. Therefore, as a material for holding an electrode, it is necessary to use a material having a water absorption rate about equal to or higher than 0 and equal to or lower than about 0.4. A material having a water absorption rate about equal to or higher than 0 and equal to or lower than about 0.25 is suitably used. Even if a material having a water absorption rate higher than 0.4 is used, it is possible to detect a signal according to sensitivity adjustment or the like. However, it is likely that the signal tends to include noise because of the high water absorption rate.

Note that, in FIG. 1, all the members of the ionization region section 5a are manufactured by a material having a low absorption rate. However, it is possible to use a material having a low water absorption rate only for a region where expiration is exposed. Specifically, a thin plate (thickness is about several mm) manufactured from a material having a low water absorption rate is stuck to the surface of another low-cost material. Consequently, it is also possible to cover, with the material having the low water absorption rate, the region where expiration is exposed. Consequently, it is possible to reduce costs of the ionization region section 5a.

Concerning a parameter of a frequency of an alternating-current voltage, a signal of expiration also has strong dependency on the parameter. Frequency dependency of expiration signal intensity is shown in FIG. 10. When the frequency is increased from 1 Hz to 100 Hz, first, observed oscillation of an expiration signal decreases. When the frequency is equal to or higher than 100 Hz, the oscillation is not substantially observed.

As an example of the expiration signal intensity, in FIGS. 11(a) and 11(b), examples of measurement of the expiration signal at the frequency of 0.1 Hz to 100 Hz are shown. It is seen that, whereas a waveform indicating a state of oscillation can be confirmed at the frequency of about 0.1 to 10 Hz, the oscillation of the expiration signal decreases from 10 Hz. This is considered to be because, since the state of the oscillation nearly disappears at the frequency of 100 Hz, when the frequency is too high, polarization and ionization of water clusters in expiration cannot follow the frequency. From the result, it is seen that, to measure the expiration signal using an alternating-current voltage, it is desirable that the frequency is set to be equal to or lower than 10 Hz and should be at least set to be equal to or lower than 100 Hz.

Note that, as a value of the alternating-current voltage is larger, the amplitude of a signal is larger and a signal having a better SN can be measured. However, as shown in FIG. 12, even if the alternating-current voltage is a voltage as low as about 1 V, the oscillation of the expiration signal can be clearly observed. Therefore, it is possible to improve safety of the sensor unit. Since measurement can be performed even at a low voltage, it is possible to realize power saving and a reduction in costs of the sensor.

As explained above, characteristics of obtained signals are greatly different in the direct-current voltage method and the alternating-current voltage method. The direct-current voltage method has a characteristic that, when an expiration time is 2 seconds, a peak of the signal can be measured in a short time (about 5 seconds). However, the signal intensity strongly depends on a state of expiration.

For example, the signal is intense in first expiration immediately after deep respiration. However, in the continuous second and third expirations, the signal intensity suddenly decreases and thereafter settles at a fixed value. Therefore, when a low voltage is set in the voltage-applied electrode, since second and third expiration signals sometimes cannot be detected, attention is necessary for measurement condition setting. On the other hand, in the alternating-current voltage method, when an expiration time is 2 seconds, it takes nearly 15 seconds to measure the entire oscillatory structure of the expiration signal. However, since the expiration signal can be stably measured without depending on a state of respiration, measurement at a low voltage is also possible. In FIG. 13, measurement examples of first and second expiration signals immediately after deep respiration in the direct-current voltage method and the alternating-current method are shown. An expiration time in the measurement examples is 2 seconds. For control of the measurement, a threshold of expiration signal intensity is set in advance, count of an expiration introduction time is started immediately after the expiration signal intensity exceeds the threshold and, when 2 second elapses, a buzzer is sounded to stop expiration introduction of the subject. This time can be arbitrarily set. However, realistically, the time is about 5 seconds at the maximum in expiration measurement. By the introduction of this simple control method, reproducibility of the expiration signal in the alternating-current voltage method is greatly improved.

As it is seen from FIG. 13, in the direct-current voltage method, expiration signal intensity in the second measurement is nearly a half of expiration signal intensity in the first measurement after deep respiration. On the other hand, in the alternating-current voltage method, it is seen that substantially the same signal intensity is obtained in the first measurement and the second measurement after deep respiration.

A reason for the high reproducibility of the expiration signal in the alternating-current voltage method can be explained as shown in FIG. 14. In general, expiration is exhaled to the outside in a state of saturated vapor pressure at 37° C. However, in the case of deep respiration, it is considered that diameter distributions of water clusters included in expiration are different in the first measurement and the subsequent measurement. In the first measurement, since a large quantity of water is present in the lung, large-diameter water clusters are also included in expiration. However, in the second and subsequent measurements, it is considered that the water in the lung slightly decreases and the large-diameter water clusters in expiration decrease.

To reduce such an intensity change of an expiration signal, detection targeting relatively small-diameter water clusters only has to be performed. For the detection, in the alternating-current voltage method, it is sufficient to polarize and ionize the water clusters in the expiration at a low frequency and a low voltage and detect a signal of the expiration.

The frequency is related to the polarization and the ionization of the water clusters and needs to be set to a low frequency equal to or lower than 100 Hz as explained above. Meaning for setting the voltage to the low voltage is explained.

A reason why it is desirable to set the voltage to the low voltage can be understood by analyzing motion in the gravity direction of water clusters having charges in motion of the water clusters having charges in an electric field. Note that, even if a direct-current voltage or an alternating-current voltage is applied between the voltage-applied electrode and the detection electrode, the motion in the gravity direction of the water clusters is represented by the same expression.

It was found by Stokes that air resistance acting on small water clusters is proportional to a radius r of a sphere and velocity $v_g$ of the sphere in the gravity direction. The magnitude of the air resistance is represented by the following expression using a coefficient of viscosity $\eta$ of the air.

Magnitude of air resistance=$6\pi\eta r v_g$

The magnitude of buoyancy by the air is equal to the gravity acting on the air excluded by the object. Therefore, in the case of the sphere having the radius r, the magnitude of the buoyancy is represented as follows using density $\rho_f$ of the air and gravitational acceleration g:

Magnitude of buoyancy by air=$(4/3)?\pi r^3 \rho_f g$

Therefore, an equation of motion of water clusters having mass m acting in the gravity direction is represented as follows:

$m(dv_g/dt)=(4/3)\pi r^3 \rho_p g - 6\pi\eta r v_g - (4/3)\pi r^3 \rho_f g$ where, $\rho_p$ is the density of water. When water clusters dropping in the air at 1 atm and 25° C. is considered, the density $\rho_p$ of water is 997.04 kg/m³, the density $\rho_f$ of the air is 1.1843 kg/m³, the coefficient of viscosity $\eta$ of the air (25° C.) is 0.0000182, and the gravitational acceleration g is 9.807 m/s². If $v_g$ is positive, the acceleration decrease to 0 as time elapses. The water clusters in the air perform uniform motion at fixed velocity. Terminal velocity $v_{g0}$ is calculated by putting the expression as zero.

$v_{g0}=2r^2(\rho_p-\rho_f)g/(9\eta)$

Therefore, when the length of the voltage-applied electrode and the detection electrode is represented as L (e.g., 0.05 m), time $t_0$ for the water clusters to reach from the upper end to the lower end of the electrode is as follows:

$$t_0 = L/v_{g0}$$
$$= 9\eta L(2r^2(\rho_p - \rho_f)g)$$

It is easily seen from this expression that, as the radius of the water clusters is larger, the water clusters reach the lower end of the electrode in a shorter time.

In FIG. 15, a change in $t_0$ at the time when the radius of the water clusters is changed from $1\times10^{-7}$ m to $1\times10^{-4}$ m is shown. Times $t_0$ at the time when the radius is $1\times10^{-4}$ m, $1\times10^{-5}$ m, $1\times10^{-6}$ m, and $1\times10^{-7}$ m can be respectively estimated as about 0.042 second, 4.2 seconds, 420 seconds, and 4200 seconds. In FIG. 16 and FIG. 17, examples of measurement of an expiration signal performed using a direct-current voltage (30 V), an alternating-current voltage (having a frequency of 1 Hz and an effective voltage of 30 V) when a blower fan provided in a lower part of an expiration sensor unit is not caused to operate are shown. An expiration time at this point is set to 2 seconds. A result of the measurement indicates time by natural drop of the water clusters. Long continuation of a signal of expiration indicates that a large number of small-radius water clusters are present.

In the case of the direct-current voltage method in FIG. 16, after expiration is introduced for 2 seconds, the signal intensity takes a maximum value after about 30 seconds, thereafter suddenly decreases, and finally decreases to zero at about 100 seconds. This is considered to indicate that a large number of water clusters having a radius of about $5\times10^{-6}$ m are detected.

On the other hand, in the case of the alternating-current voltage in FIG. 17, after expiration is introduced for 2 seconds, the signal intensity gradually increases to take a maximum value after about 30 seconds and finally decreases to zero at about 200 seconds. This is considered to indicate that a large number of relatively small water clusters of about $1\times10^{-6}$ m are detected and the radius of the detected water clusters is smaller than that in the case of the direct-current voltage method. Relatively large water clusters depend on a state of respiration, that is, a large number of the water clusters are included in expiration immediately after deep respiration. However, it is estimated that the water clusters are dried more or less in continuous expiration after that and the number of the water clusters decreases. Therefore, the direct-current voltage method in which relatively large water clusters are a detection target is considered to be susceptible to this influence.

On the other hand, in the alternating-current voltage method, since relatively small water clusters are a detection target, the alternating-current voltage method is considered to be less susceptible to this influence and improve reproducibility of an expiration signal. Judging from an SN of the present expiration signal, an effective voltage in the alternating-current voltage method can be detected even if the effective voltage is reduced to 0.1V. On the other hand, there is no upper limit in the level of the effective voltage in the alternating-current voltage method. However, 600 V for defining a high voltage in an alternating current is one reference.

In this embodiment, the direct-current voltage and the alternating-current voltage are used and the gravity direction is important. Therefore, it is important to adopt a configuration for enabling outside air such as expiration to pass through a space (an ionization region) formed between the voltage-applied electrode 6c and the detection electrode 7c. Further, the voltage-applied electrode 6c and the detection electrode 7c are preferably arranged side by side with respect to the gravity direction and more preferably arranged substantially parallel to each other.

It is effective in the following points to configure the detection system to be capable of applying the direct-current voltage to the voltage-applied electrode 6 in addition to the alternating-current voltage and switching the direct-current voltage and the alternating-current voltage each other. Specifically, the detection system is configured to control to switch a sensor power supply 15 with the measurement control unit 17 and apply a desired voltage to the voltage-applied electrode 6 from the sensor power supply 15. As explained above, when the direct-current voltage is used, the relative large water clusters can be set as a measurement target. Therefore, after measurement is performed at the alternating-current voltage having high reproducibility of signal intensity, it is possible to switch the alternating-current voltage to the direct-current voltage, exclude the water clusters present inside the ionization region in a short time, and prepare for the next measurement.

In the alternating-current voltage method, a signal of expiration oscillating according to the frequency of the alternating-current voltage is observed. This proves that the expiration is human respiration including very small water clusters passing through the respiratory tract and generated. In general, when the sectional area of the ionization region is represented as A, a rate of inflow of expiration is represented as $q_i$, and a rate of outflow of expiration is represented as $q_o$, the following expression holds concerning an amount $\Delta h(t)$ of expiration present in the ionization region in a very short time $\Delta t$:

$$A \cdot \Delta h(t) = (q_i - q_o) \cdot \Delta t$$

In an equilibrium state, since there is no change in an amount of expiration, $q_i = q_o$. It is assumed that an amount of expiration caused to flow into the ionization region is increased by $\Delta q$ from the equilibrium state. When the resistance on the outflow side is represented as R, the following expression holds:

$$\Delta q_o(t) = (1/R) \cdot \Delta h(t)$$

From the above two expressions, the following expression is derived:

$$\Delta h(t) = R \cdot \Delta q \cdot (1 - e^{-t/\tau}) \tau = A \cdot R$$

For example, when it is assumed that expiration to be introduced is a rectangular wave having width of 2 seconds, an expiration signal waveform obtained from an expiration signal should be approximately observed in a form shown in FIG. 18. An example of a change with time of peak intensities of an oscillatory structure in the alternating-current voltage method (at an expiration time of 2 seconds, a frequency of 1 Hz, and an effective voltage of 30 V and with only a positive ion peak) is shown in FIG. 19. In this case, it is seen that the signal intensity is nearly saturated in 4 seconds after signal detection and linearly decreases after 4 seconds. Note that the ionization region at this point has width of 10 mm, depth of 15 mm, height of 40 mm, and a volume of 6000 mm$^3$.

When the expiration time is specified in this way, a change in this signal can be used for a determination algorithm for expiration. That is, for example, (1) time until the signal intensity is saturated and (2) an intensity change until the signal intensity is saturated is described by an exponential function $1 - e^{-t/\tau}$. Note that, when the expiration time is 2 seconds, measurement of the entire oscillatory structure takes about 8 seconds. However, when the above examination is taken into account, a measurement time only has to be substantially 4 seconds.

Vapor from a heated container or a signal from an artificial atomizer such as an ultrasonic humidifier can be excluded when the algorithm is used. Further, it is also possible to calculate a relation between a signal value of an alcohol sensor such as a semiconductor sensor and an expiration signal and correct alcohol concentration from the expiration signal. The amplitude in the expiration signal is proportional to time and an amount of expiration. When the amplitude is equal to or higher than a certain level, this proves that sufficient expiration is introduced into the sensor unit. This can prevent circumvention of the law from being committed to reduce an alcohol value in an alcohol test or the like without introducing sufficient expiration into the sensor unit.

In FIG. 20, a difference in signal intensity according to a distance from the sensor is shown. In the expiration sensor, such strong distance dependency can be given to the signal intensity. Therefore, by providing a setting place of the expiration sensor near a window on a driver side, it is possible to prevent a masquerade in which a person different from the driver carries out a test during a stop or during traveling of a car.

An evaluation by a drinking test was performed taking into account the examination result. A person drank 200 cc of 10% alcohol for 5 minutes. A change with time in about 2 hours of an expiration alcohol amount was measured. Basically, the alcohol was measured by a semiconductor alcohol sensor. A comparison by measurement in an electrochemical system considered to have high selectivity to ethanol and having high measurement accuracy was also performed. An alternating-current detection method based on control of an expiration introducing time and securing of time in which the semiconductor alcohol sensor is stabilized was used. Consequently, data in which a measurement result of the semiconductor alcohol sensor and a measurement result by the electrochemical system substantially coincided with each other was able to be acquired.

A comparison result of the measurement results is shown in FIG. 21. For reference, a detection result of an expiration signal and an alcohol signal for measuring a change with time is shown in FIG. 22. This is data after 15 minutes after the drinking.

Note that, in the semiconductor alcohol sensor that measures an electrical conductivity change due to gas absorption on the surface of a metal oxide semiconductor, signal intensity strongly depends on parameters such as pressure on the sensor surface. When alcohol having concentration in a certain fixed range is measured by the semiconductor sensor, it is effective to always form a fixed flow of the air on the surface of the semiconductor alcohol sensor and carry out measurement in the flow of the air taking into account the high pressure dependency. According to this operation, a base line of the semiconductor alcohol sensor is stabilized. For that purpose, in a simple sense, it is effective to arrange the semiconductor alcohol sensor head 3a in the detection electrode 7a via an electric insulation material as shown in FIG. 1 in the ionization region section 5a surrounded by the voltage-applied electrode 6a, the detection electrode 7a, and the material, the water absorption rate of which is zero. When the semiconductor alcohol sensor head 3a is arranged, a hole for gas is provided in the detection electrode such that expiration easily reaches the surface of the semiconductor alcohol sensor. In the ionization region of the sensor unit, a flow of the air is always generated by the fan 4a provided in the lower part of the sensor unit. Compared with the case in which the semiconductor alcohol sensor is set in a completely open state, the base line can be stabilized earlier when the semiconductor alcohol sensor is placed in a region where a fixed flow of the air is always present. Usually, it is possible to stabilize the base line of the semiconductor sensor in about 2 to 3 minutes by providing a fan having an air capacity of about 0.01 m$^3$/minute to form a fixed air flow.

This change with time is shown in FIG. 23. Therefore, when the fan is driven and the sensor unit is actually caused to operate from a state in which the sensor unit is not caused to operate, stable data is acquired if measurement is started after the fan is driven for about 2 to 3 minutes. On the other hand, in a state in which the fan is driven, measurement can be immediately performed.

Second Embodiment

In general, about 20% of alcohol (ethanol) taken into the body by drinking is absorbed from the stomach and about 80% of the alcohol is absorbed from the small intestine. Then, the alcohol enters the blood and spreads to the entire body. Most of the alcohol taken into the body is metabolized in the liver. Most of the alcohol reaching the liver is metabolized in the liver to change to acetaldehyde. The acetaldehyde is further oxidized into acetic acid in the liver. Apart of the acetic acid is carried to tissues of the entire body by the blood flow and converted into acetyl CoA in peripheral muscle tissues and the like, enters a citric acid cycle, and finally changes to water and carbon dioxide while producing energy. 2 to 10% of the absorbed alcohol is directly discharged to the outside of the body by expiration, urine, and sweat without being metabolized. Blood alcohol concentration is in a proportional relation with expiration alcohol concentration. The expiration alcohol is observed as one of excretions of alcohol after the drinking. Therefore, when a person drinks alcohol, the alcohol is finally discharged to the outside of the body as water, carbon dioxide, and alcohol.

Water at a saturated vapor pressure level at about 37° C. is included in expiration. Therefore, the water in the expiration substantially changes to water clusters and is discharged to the outside of the body. Therefore, when the person drinks the alcohol, carbon dioxide, alcohol, and the like are included in the water clusters in the aspiration. At this point, apart of the carbon dioxide dissolved in the water changes to carbonic acid.

$$CO_2 + H_2O \leftrightarrow H_2CO_3 \quad \text{[Chemical 1]}$$

The carbonic acid causes dissociation of two stages in a water solution.

$$CO_2 + H_2O \leftrightarrow H^+ + HCO_3^- \quad \text{[Chemical 2]}$$

$$HCO_3^- \leftrightarrow H^+ + CO_3^{2-} \quad \text{[Chemical 3]}$$

Therefore, when the person drinks the alcohol, it is considered that negative ions are generated in a state in which a large number of water clusters in the expiration are present.

The merit of reducing the alternating-current voltage is also proved from the following points. In FIG. 24, an alcohol metabolic process is shown. When the person drinks the alcohol, unmetabolized alcohol is discharged in addition to water and carbon dioxide, which are final metabolic products. In a normal expiration alcohol test, a test of expiration alcohol proportional to blood alcohol concentration is performed. However, since carbon dioxide, which is a product of the drinking of the alcohol, is also discharged, $HCO_3^-$ or $CO_3^{2-}$ is observed as negative ions according to the dissociation in the water solution. Although carbon dioxide is also included in normal expiration, negative ion intensity after alcohol drinking is observed high. When a condition under which peaks of the negative ions are observed is calculated, it is seen that the negative ion peaks are observed at a frequency equal to or lower than 1 Hz and an effective voltage equal to or lower than 10 V in the alternating-current detection. What are interesting in the negative ion peaks observed simultaneously with expiration introduction are two points: the intensity of the negative ion peaks observed in first measurement immediately after deep respiration is high and, when second and third measurements are continuously performed, the intensity decreases and the negative ion peaks finally disappear; and the negative ion peaks are observed even if a voltage is not applied to a voltage-applied electrode.

As an evident that the negative ion peaks are observed even if a voltage is not applied, in FIG. 25, a negative ion peak observed in the first measurement immediately after deep respiration is shown. In this case, although exhaust by a fan is performed, a voltage is not applied. However, for an evidence that the negative ion peak is a peak in expiration, it is necessary to apply an alternating-current voltage and measure an oscillating signal.

The intensity of the negative ion peak has a correlation with a change with time of expiration alcohol. An example of the correlation is shown in FIG. 26. This is an example in which, for 2 hours after a person drinks 200 cc of 10% alcohol, an intensity change of negative ion peaks is observed together with a change in an output by a semiconductor sensor. It is seen that a state in which the expiration alcohol reaches the maximum in about 30 minutes after the drinking and thereafter decreases according to metabolism is observed in an intensity change of the negative ion peaks observed simultaneously with the expiration introduction as in the semiconductor sensor. When an intensity change of a negative current involved in the negative ions is plotted, it is seen that the intensity change is similar to a change with time by an alcohol sensor in an electrochemical system measured simultaneously with the intensity change and indicates a change in alcohol metabolism. The intensity of the negative current involved in the negative ions depends on an amount of drunken alcohol. However, since the alternating-current voltage is equal to or smaller than about several volts, when the intensity of an oscillatory structure involved in expiration is high, the oscillatory structure overlaps. Therefore, from this viewpoint, it is desirable that the alternating-current voltage is equal to or lower than 100 V and is suitably about 1 to 5 V.

When the detection method for detecting alcohol using the alternating-current power supply is used, it is unnecessary to use the alcohol sensor. This is a great merit in terms of a reduction in costs and simplicity of a structure.

Third Embodiment

As explained above, in the alternating-current detection method, ionized water clusters oscillate according to a frequency at which an expiration signal is applied. An induction current generated by the oscillation is detected. Compared with when a main substance included in expiration is water clusters, when a large amount of alcohol is included in expiration, the number of ionized water clusters decreases. Therefore, the decrease should be observed.

An example showing this difference is shown in FIG. 27. The horizontal axis indicates the order of peaks of an oscillatory structure observed by the alternating-current detection method. The vertical axis indicates the intensity of the peaks. The intensities of the peaks of the oscillatory structure involved in the expiration not including alcohol are plotted by diamond markers. The intensities of the peaks of the oscillatory structure involved in the expiration including alcohol are plotted by square markers. Expiration alcohol of the expiration including alcohol was 0.15 mg/L when measured by the electrochemical system. It is seen that, at a stage when expiration is introduced, substantially the same intensity is observed under a condition of the same expiration time (3 seconds) irrespective of presence or absence of alcohol but, in a process in which the expiration is exhausted by an exhaust fan, compared with the peaks of the oscillatory structure involved in the expiration not including alcohol, in the peaks of the oscillatory structure involved in the expiration including alcohol, the intensity decreases between 10 and 20 in the order of the peaks. Even if the semiconductor alcohol sensor is not used, it is possible to easily measure presence or absence of alcohol in expiration in such a form.

The present invention can be used for noncontact and noninvasive expiration detection. The present invention can also be used for a drunken driving prevention apparatus in a mobile body such as an automobile.

REFERENCE SIGNS LIST

1a Sensor unit
1b Sensor unit
1c Sensor unit
2a Sample introducing port
2b Sample introducing port
2c Sample introducing port
2d Sample introducing port
3a Alcohol sensor head
3b Alcohol sensor head
3c Alcohol sensor head
4a Exhaust fan
4b Exhaust fan
4c Exhaust fan
5a Ionization region section
5b Ionization region section
6a voltage applied-electrode
6b voltage applied-electrode
6c voltage applied-electrode
7a Detection electrode
7b Detection electrode
7c Detection electrode
8 Voltage-applied electrode holder
9 Detection electrode holder
10 Alcohol detection hole
11 Alcohol sensor support hole
12 Sensor cover
13a Exhaust port
13b Exhaust port
14a Cable
14b Cable
14c Cable
14d Cable
15a Sensor power supply
15b Sensor power supply
16a Sensor amplifier
16b Sensor amplifier
17 Measurement control unit
18 Memory card slot
19 Indicator lamp
20 GPS antenna unit
21 Power inverter
22 Alcohol sensor amplifier
23a CPU
23b CPU
24a Power supply
24b Power supply
25 GPS antenna
26 GPS receiver
27 Memory card interface
28 Speaker
29 Insulating material

The invention claimed is:

1. An outside air detecting apparatus comprising:
a housing under an atmospheric pressure having an introducing port for introducing outside air into the housing;
a voltage applied-electrode disposed in the housing;
a detection electrode disposed in the housing,
wherein the outside air introduced into the housing through the introducing port passes between the voltage applied-electrode and the detection electrode;
an outlet for discharging the outside air that passes between the voltage applied-electrode and the detection electrode from the housing to outside;
an alcohol sensor disposed in the housing;
a power supply configured to apply a voltage to the voltage applied-electrode;
a measurement control unit having a memory and a processor which are configured to control the voltage applied from the power supply to the voltage applied-electrode and to measure a signal from a current detected by the detection electrode; and
an output unit configured to output a measurement based on the signal,
wherein the detection electrode and the voltage-applied electrode face each other,
wherein the detection electrode detects current generated by the outside air that passes between the voltage applied electrode and the detection electrode by the application of an alternating-current voltage to the voltage-applied electrode,
wherein the measurement control unit measures the signal from the current detected by the detection electrode for a predetermined period of time after an intensity of the signal exceeds a predetermined threshold stored in the memory, and the output unit outputs the measurement based on the signal, and
wherein the measurement control unit measures an alcohol signal from the alcohol sensor and the signal from the current detected by the detection electrode.

2. The outside air detecting apparatus according to claim 1, wherein the power supply is configured to switch between the alternating-current voltage and a direct-current voltage, and
wherein the measurement control unit applies the alternating-current voltage and measures a signal from the current from the detection electrode, and after detecting the signal, the measurement control unit applies the direct-current voltage to the voltage applied-electrode.

3. The outside air detecting apparatus according to claim 1,
wherein the alcohol sensor is a semiconductor sensor having a detection surface that is exposed to the air.

4. The outside air detecting apparatus according to claim 1, wherein a frequency of the alternating-current voltage applied to the voltage applied-electrode is equal to or lower than 100 Hz.

5. The outside air detecting apparatus according to claim 1, wherein the alternating-current voltage applied to the voltage applied-electrode is equal to or lower than 100 V.

6. The outside air detecting apparatus according to claim 3, further comprising:
a fan,
wherein the detection surface of the semiconductor sensor is arranged in a channel, which has the introduced outside air.

7. The outside air detecting apparatus according to claim 2, wherein the alcohol sensor is a semiconductor sensor having a detection surface that is exposed to the air.

8. The outside air detecting apparatus according to claim 1, wherein the measurement control unit stores in the memory and executes a determination algorithm having a time until the signal is saturated and an intensity change until the signal is saturated described by an exponential function $1-e^{-t/\tau}$, and
wherein the output unit outputs a determination based on the determination algorithm.

9. The outside air detecting apparatus according to claim 1, wherein the alternating-current voltage applied to the voltage applied electrode is equal to and higher than 0.1 V and equal to and lower than 600V.

10. The outside air detecting apparatus according to claim 1, wherein a frequency of the alternating-current voltage applied to the voltage applied-electrode is equal to or lower than 10 Hz.

11. The outside air detecting apparatus according to claim 1, wherein the alternating-current voltage applied to the voltage applied-electrode is equal to or lower than 5V.

12. The outside air detecting apparatus according to claim 1, wherein the memory has a correlation between the signal and the alcohol signal, and the measurement control unit corrects an alcohol concentration based on the correlation.

13. The outside air detecting apparatus according to claim 1, wherein the alcohol sensor is disposed in a flow of the air.

14. An outside air detecting apparatus, comprising:
a housing under an atmospheric pressure having an introducing port for introducing outside air into the housing;
a voltage applied-electrode disposed in the housing;
a detection electrode disposed in the housing,
wherein the outside air introduced into the housing through the introducing port passes between the voltage applied-electrode and the detection electrode;
an outlet for discharging the outside air that passes between the voltage applied-electrode and the detection electrode from the housing to outside;
a power supply configured to apply a voltage to the voltage applied-electrode,
a measurement control unit having a memory and a processor which are configured to control the voltage applied from the power supply to the voltage applied-electrode and to measure a signal from a current detected by the detection electrode,
an output unit configured to output a measurement based on the signal,
wherein the detection electrode and the voltage-applied electrode face each other,
wherein the detection electrode detects current generated by the outside air that passes between the voltage applied electrode and the detection electrode by the application of an alternating-current voltage to the voltage-applied electrode, and
wherein the measurement control unit measures the signal from the current detected by the detection electrode for a predetermined period of time after an intensity of the signal exceeds a predetermined threshold stored in the memory, and the output unit outputs the measurement based on the signal; and
a semiconductor sensor, at least a detection surface of which is disposed in the housing such that at least the detection surface is exposed to the introduced outside air,
wherein a hole section is formed in a part of the detection electrode and the detection surface of the semiconductor sensor is arranged in the hole section to expose the detection surface.

15. The outside air detecting apparatus according to claim 1, wherein the detection electrode and the voltage applied-electrode are arranged side by side with respect to a direction of the force of gravity.

* * * * *